United States Patent
Pomper et al.

(10) Patent No.: US 9,044,468 B2
(45) Date of Patent: Jun. 2, 2015

(54) LABELED INHIBITORS OF PROSTATE SPECIFIC MEMBRANE ANTIGEN (PSMA), BIOLOGICAL EVALUATION, AND USE AS IMAGING AGENTS

(75) Inventors: Martin G. Pomper, Baltimore, MD (US); Ray Sangeeta, Ellicott City, MD (US); Ronnie C. Mease, Fairfax, VA (US); Catherine Foss, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1121 days.

(21) Appl. No.: 12/666,441

(22) PCT Filed: Jun. 26, 2008

(86) PCT No.: PCT/US2008/007947
§ 371 (c)(1),
(2), (4) Date: Nov. 22, 2010

(87) PCT Pub. No.: WO2009/002529
PCT Pub. Date: Dec. 31, 2008

(65) Prior Publication Data
US 2011/0064657 A1 Mar. 17, 2011

Related U.S. Application Data

(60) Provisional application No. 60/937,242, filed on Jun. 26, 2007, provisional application No. 61/011,111, filed on Jan. 15, 2008.

(51) Int. Cl.
| | |
|---|---|
| *A61K 51/04* | (2006.01) |
| *A61K 31/513* | (2006.01) |
| *A61K 31/4402* | (2006.01) |
| *A61K 31/145* | (2006.01) |
| *A61K 31/195* | (2006.01) |
| *A61K 31/395* | (2006.01) |
| *A61K 38/06* | (2006.01) |
| *C07D 213/38* | (2006.01) |
| *C07D 215/12* | (2006.01) |
| *C07D 257/00* | (2006.01) |
| *G01N 33/574* | (2006.01) |

(52) U.S. Cl.
CPC ........... *A61K 31/4402* (2013.01); *A61K 31/145* (2013.01); *A61K 31/195* (2013.01); *A61K 31/395* (2013.01); *A61K 38/06* (2013.01); *A61K 51/0402* (2013.01); *C07D 213/38* (2013.01); *C07D 215/12* (2013.01); *C07D 257/00* (2013.01); *G01N 33/57434* (2013.01); *G01N 2500/04* (2013.01)

(58) Field of Classification Search
USPC ............... 424/9.1, 139.1, 1.69; 514/100, 115, 514/120, 121, 332, 588, 595; 548/113, 253
See application file for complete search history.

(56) References Cited

U.S. PATENT DOCUMENTS

| | | | |
|---|---|---|---|
| 6,875,886 B2 * | 4/2005 | Frangioni | 560/171 |
| 2003/0138432 A1 | 7/2003 | Glazier | |
| 2004/0054190 A1 * | 3/2004 | Pomper et al. | 548/253 |
| 2007/0031326 A1 | 2/2007 | Shirvan et al. | |
| 2008/0193381 A1 * | 8/2008 | Babich et al. | 424/9.1 |

FOREIGN PATENT DOCUMENTS

| | | |
|---|---|---|
| WO | 03/000201 A2 | 1/2003 |
| WO | 2008/057437 A2 | 5/2008 |
| WO | 2008/058192 A2 | 5/2008 |
| WO | 2008/121949 A1 | 10/2008 |

OTHER PUBLICATIONS

S. Jayaprakash et al., "Design and Synthesis of a PSMA Inhibitor-Doxorubicin Conjugate for Targeted Prostate Cancer Therapy", Chem Med. Chem., vol. 1, pp. 299-302 (2006).
K. Schlogl et al., "Konstitutionsermittlung von Peptiden. VI. Lysylpeptide", Monatshefte Fur Chemie, 84(5), pp. 937-955 (1953).
S. Umezawa et al., "Strucute of Antipain, A New Sakaguchi-Positive Product of *Streptomyces*", Journal of Antibiotics, Japan Antibiotics Research Association, Tokyo, JP, 25(4), pp. 267-270 (1972)—XP008017839.
Y. Konda et al., "First total synthesis of Mer-N5075A and a diastereomeric mixture of alpha and beta-MAPI, new HIV-I protease inhibitors from a species of *Streptomyces*", Tetrahedron, Elsevier Science Publishers, Amsterdam, NL, 57(2), pp. 4311-4321 (2001).
Foss et al., "Radiolabeled Small-Molecule Ligands for Prostate-Specific Membrane Antigen: In vivo Imaging in Experimental Models of Prostate Cancer", Clin. Cancer Res., vol. 11(11) (2005).

\* cited by examiner

*Primary Examiner* — Michael G Hartley
*Assistant Examiner* — Jagadishwar Samala
(74) *Attorney, Agent, or Firm* — Ward and Smith, P.A.

(57) ABSTRACT

The prostate-specific membrane antigen (PSMA) is increasingly recognized as a viable target for imaging and therapy of cancer. Various 99mTc/Re-labeled compounds were prepared by attaching known Tc/Re chelating agents to an amino-functionalized PSMA inhibitor with or without a variable length linker moiety. Ex vivo biodistribution and in vivo imaging demonstrated the degree of specific binding to engineered PSMA+ PC3 PIP tumors.

4 Claims, 6 Drawing Sheets

LABELED INHIBITORS OF PROSTATE SPECIFIC MEMBRANE ANTIGEN (PSMA), BIOLOGICAL EVALUATION, AND USE AS IMAGING AGENTS

RELATED APPLICATIONS

This application is a 35 U.S.C. §371 U.S. national entry of International Application PCT/US2008/007947 (WO 2009/002529) and claims the benefit of U.S. Provisional Application Ser. No. 60/937,242, filed Jun. 26, 2007, and U.S. Provisional Application Ser. No. 61/011,111, filed Jan. 15, 2008, the teachings of which are incorporated herein by reference.

BACKGROUND OF THE INVENTION

1. Field of the Invention

The present invention provides novel compounds comprising a urea derivative, a linker, and a metal chelating group. The invention provides for novel radiolabeled compounds comprising a urea derivative, a linker, a metal chelating group, and a radiolabeled or isotopically labeled metal. This invention also provides pharmaceutical compositions comprising such radiolabeled compounds. Additionally, this invention provides methods of detecting biodistribution and imaging methods of the compounds of the invention which bind to PSMA and PSMA expressing tumors. The compounds of the invention are useful for providing an earlier diagnosis of cancers, imaging tumor angiogenesis, improved delineation of tumor margins during tumor surgery, and improvements in small molecule delivery of therapeutic radionuclides to cancer.

2. Background

Prostate cancer (PCa) is the leading cancer in the US population and the second leading cause of cancer-related death in men. By the time of diagnosis only one half of PCa tumors are clinically localized and one half of those represent extracapsular spread. Currently anatomic methods, such as computed tomography (CT), magnetic resonance (MR) imaging and ultrasound, predominate for clinical imaging of prostate cancer. The radiolabeled monoclonal antibody [$^{111}$In]ProstaScint™ has also been used, however this agent tends to produce images that are challenging to interpret (Lange, P. H. PROSTASCINT scan for staging prostate cancer. *Urology* 2001, 57, 402-406; Haseman, M. K.; et al. *Cancer Biother Radiopharm* 2000, 15, 131-140; Rosenthal, S. A.; et al. *Tech Urol* 2001, 7, 27-37). Low molecular weight, radiopharmaceutical-based imaging agents may provide superior pharmacokinetics for imaging than radiolabeled antibodies, which tend to have long circulation times and delayed clearance from nontarget tissues. A variety of experimental low molecular weight PCa imaging agents are currently being pursued clinically, including radiolabeled choline analogs [$^{18}$F]fluorodihydrotestosterone ([$^{18}$F]FDHT), anti-1-amino-3-[$^{18}$F]fluorocyclobutyl-1-carboxylic acid (anti[$^{18}$F]F-FACBC), [$^{11}$C]acetate and 1-(2-deoxy-2-[$^{18}$F]fluoro-L-arabinofuranosyl)-5-methyluracil ([$^{18}$F]FMAU) (Scher, B.; et al. *Eur J Nucl Med Mol Imaging* 2007, 34, 45-53; Rinnab, L.; et al. *BJU Int* 2007, 100, 786-793; Reske, S. N.; et al. *J Nucl Med* 2006, 47, 1249-1254; Zophel, K.; Kotzerke, J. *Eur J Nucl Med Mol Imaging* 2004, 31, 756-759; Vees, H.; et al. *BJU Int* 2007, 99, 1415-1420; Larson, S. M.; et al. *J Nucl Med* 2004, 45, 366-373; Schuster, D. M.; et al. *J Nucl Med* 2007, 48, 56-63; Tehrani, O. S.; et al. *J Nucl Med* 2007, 48, 1436-1441).

Each operates by a different mechanism and has certain advantages, e.g., low urinary excretion for [$^{11}$C]choline, and disadvantages, such as the short physical half-life of positron-emitting radionuclides. A promising new series of low molecular weight imaging agents targets the prostate-specific membrane antigen (PSMA) (Mease R. C. et al. *Clin Cancer Res.* 2008, 14, 3036-3043; Foss, C. A.; et al. *Clin Cancer Res* 2005, 11, 4022-4028; Pomper, M. G.; et al. *Mol Imaging* 2002, 1, 96-101; Zhou, J.; et al. *Nat Rev Drug Discov* 2005, 4, 1015-1026).

PSMA is a type II integral membrane protein that has abundant and restricted expression on the surface of PCa, particularly in androgen-independent, advanced and metastatic disease (Schulke, N.; et al. *Proc Natl Acad Sci USA* 2003, 100, 12590-12595). The latter is important since almost all PCa becomes androgen independent. It is also expressed within the endothelium of most solid tumors other than prostate (Chang, S. S.; et al. *Cancer Res* 1999, 59, 3192-3198). PSMA possesses the criteria of a promising target for therapy, i.e., abundant and restricted (to prostate) expression at all stages of the disease, presentation at the cell surface but not shed into the circulation, and association with enzymatic or signaling activity (Schulke, N.; et al. *Proc Natl Acad Sci USA* 2003, 100, 12590-12595). The PSMA gene is located on the short arm of chromosome 11 and functions both as a folate hydrolase and neuropeptidase. It is the neuropeptidase function that is equivalent to glutamate carboxypeptidase II (GCPII), which is referred to as the "brain PSMA", and may modulate glutamatergic transmission by cleaving N-acetylaspartylglutamate (NAAG) to N-acetylaspartate (NAA) and glutamate (Nan, F.; et al. *J Med Chem* 2000, 43, 772-774). There are up to $10^6$ PSMA molecules per cancer cell, further suggesting it as an ideal target for imaging and therapy with radionuclide-based techniques (Tasch, J.; et al. *Crit Rev Immunol* 2001, 21, 249-261).

Recently selective imaging was demonstrated of xenografts that express PSMA using small animal positron emission tomography (PET) and single photon emission computed tomography (SPECT) and the urea-based PSMA inhibitors N—[N—[(S)-1,3-dicarboxypropyl]carbamoyl]-(S)—[$^{11}$C]methyl-L-cysteine, [$^{11}$C]DCMC, N—[N—[(S)-1,3-dicarboxypropyl]carbamoyl]-(S)-3-[$^{125}$I]iodo-L-tyrosine, [$^{125}$I]DCIT and N—[N—[(S)-1,3-dicarboxypropyl]carbamoyl]-(S)-4-[$^{18}$F]fluorobenzyl-L-cysteine, [$^{18}$F]DCFBC (Mease R. C. et al. Clin Cancer Res. 2008, 14, 3036-3043; Foss, C. A.; et al. *Clin Cancer Res* 2005, 11, 4022-4028; Pomper, M. G.; et al. *Mol Imaging* 2002, 1, 96-101).

Although positron-emitting radionuclides are increasingly used in clinical medicine, $^{99m}$Tc remains the radionuclide of choice for clinical scintigraphic imaging because of its favorable physical properties ($t_{1/2}$=6 h, $E_\gamma$=140 keV), low cost and widespread availability. The development of technetium complexes as radiopharmaceuticals is facilitated by the use of rhenium, the group VIIB congener of technetium. Rhenium generally produces complexes with similar physical properties to those of technetium and is often used as a nonradioactive alternative to technetium for large-scale synthesis and structural characterization.

What is desired is to provide low molecular weight, urea-based inhibitors incorporating tridentate chelators for binding of the {M(CO)$_3$}$^+$ core, (M=$^{99m}$Tc, $^{186, 188}$Re), while retaining high affinity to PSMA. Because of high stability and favorable labeling characteristics, the organometallic Re(I)(CO)$_3$/$^{99m}$Tc(I)(CO)$_3$ approach represents an attractive radiolabeling strategy. A number of tridentate chelates with different sets of nitrogen, sulfur, oxygen donor atoms are known to form highly stable complexes with the {M(CO)$_3$}$^+$ cores (Alberto, R.; et al. *J Am Chem Soc* 1998, 120, 7987-7988; Alberto, R.; et al. *J Am Chem Soc* 2001, 123, 3135-3136). Among them, the single amino acid chelate concept (Banerjee, S. R.; et al. *Nucl Med Biol* 2005, 32, 1-20; Stephenson, K. A.; et al. *Bioconjug Chem* 2005, 16, 1189-1195), (SAAC), has proved useful for designing new urea-based inhibitors.

SUMMARY OF THE INVENTION

In one aspect, the invention provides a compound comprising an inhibitor, a linker, and a metal chelator.

In another aspect, the invention provides a compound of formula I:

  (I)

wherein A is a metal chelator; B is a linker; C is a PSMA inhibitor; and b is 1-5.

In certain embodiments, the invention provides a compound of formula II:

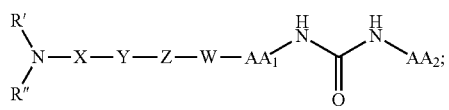  (II)

wherein

R' is —CO—NR$^x$R$^y$—, —CS—NR$^x$R$^y$—, COR$^x$, CSR$^x$, C(NR$^x$)R$^x$, —S(O)$_p$R$^x$—, —CO$_2$—NR$^x$R$^y$—, or optionally substituted alkyl;

R" is H or optionally substituted alkyl;

R$^x$ is optionally substituted aryl or optionally substituted alkyl;

R$^y$ is H, optionally substituted aryl or optionally substituted alkyl;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y and W are each independently —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

$R_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl.

In other embodiments, the invention provides a compound of formula III:

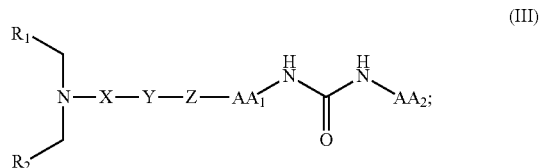  (III)

wherein $R_1$ and $R_2$ are each independently selected from optionally substituted aryl, optionally substituted heteroaryl, optionally substituted heterocyclo, —COOH, hydroxyl, optionally substituted alkoxy, amino, optionally substituted mono or dialkylamino, thiol, and optionally substituted alkylthiol;

AA$_1$ and AA$_2$ are each independently a natural or unnatural amino acid;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y is —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

$R_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl.

In certain embodiments, the invention provides a compound of formula IV:

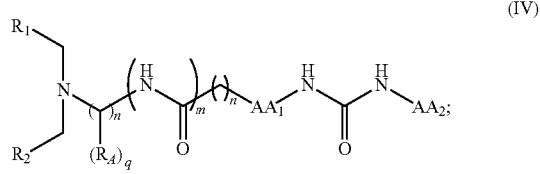  (IV)

wherein

AA$_1$ and AA$_2$ are each independently a natural amino acid;

$R_1$ is pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl;

$R_2$ is pyridyl, pyrimidinyl, pyrazinyl, pyridizinyl, quinolinyl, thienyl, thiazolyl, oxazolyl, isoxazolyl, pyrrolyl, furanyl, isoquinolinyl, or triazolyl, —COOH, hydroxyl, alkoxy, amino, mono or dialkylamino;

$R_A$, for each occurrence, is halogen, hydroxy, amino, cyano, nitro, or $CO_2H$;

m is 0 or 1;

each n is independently 1-8; and each q is independently 0 or 1.

In one embodiment, the invention provides for a compound of formula V:

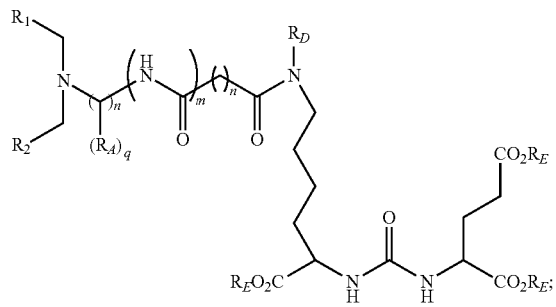

(V)

wherein each $R_D$ is independently H, optionally substituted alkyl, optionally substituted cycloalkyl, optionally substituted aryl, optionally substituted heteroaryl, optionally substituted heterocyclo, or optionally substituted aralkyl;

each $R_E$ is independently H, optionally substituted alkyl, optionally substituted cycloalkyl, optionally substituted aryl, optionally substituted heteroaryl, optionally substituted heterocyclo, or optionally substituted aralkyl;

$R_1$ is pyridyl, pyrimidinyl, pyrazinyl, pyridizinyl, isoquinolinyl, imiazolyl, or quinolinyl;

$R_2$ is pyridyl, pyrimidinyl, pyrazinyl, pyridizinyl, isoquinolinyl, quinolinyl; —COOH, hydroxyl, alkoxy, amino, mono or dialkylamino;

$R_A$, for each occurrence, is hydroxy, amino, or $CO_2H$;

each m is independently 0 or 1; and each n is independently 1-8.

In another embodiment, the invention provides a compound of formula VI:

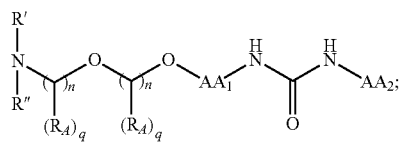

(VI)

wherein $AA_1$ and $AA_2$ are each independently a natural amino acid;

R' is —CO—$NR^xR^y$—, —CS—$NR^xR^y$—, $COR^x$, $CSR^x$, $C(NR^x)R^x$, —$S(O)_pR^x$—, —$CO_2$—$NR^xR^y$—, or optionally substituted alkyl;

R" is H or optionally substituted alkyl;

$R^x$ is optionally substituted aryl or optionally substituted alkyl;

$R^y$ is H, optionally substituted aryl or optionally substituted alkyl;

$R_A$, for each occurrence, is halogen, hydroxy, amino, cyano, nitro, or $CO_2H$;

each n is independently 0-8; and each q is independently 0 or 1.

In another embodiment, the invention provides a compound of formula VII:

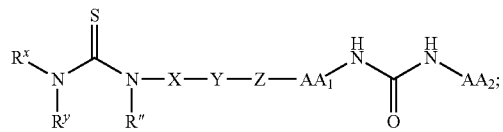

(VII)

wherein

R" is H or optionally substituted alkyl;

$R^x$ is optionally substituted aryl or optionally substituted alkyl;

$R^y$ is H, optionally substituted aryl or optionally substituted alkyl;

$AA_1$ and $AA_2$ are each independently a natural or unnatural amino acid;

X and Z are each independently $C_1$-$C_8$ alkyl, $C_2$-$C_8$ alkenyl, or $C_2$-$C_8$ alkynyl, $C_1$-$C_8$ heteroalkyl, $C_2$-$C_8$ heteroalkenyl, or $C_2$-$C_8$ heteroalkynyl, $C_1$-$C_8$ alkoxy, or a bond, each of which may be substituted with 0-5 $R_A$;

Y is —O—, —$S(O)_p$—, —NH—, —$NR_B$—, —CH=CH—, —$CR_B$=CH—, —CH=$CR_B$—, —NH—CO—, —NH—$CO_2$—, —$NR_B$—CO—, —$NR_B$—$CO_2$—; —CO—NH—, —$CO_2$—NH—, —CO—$NR_B$—, —$CO_2$—$NR_B$—, or a bond;

p is 0, 1, or 2;

$R_A$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl.

In one embodiment, the invention provides a compound of formula VIII:

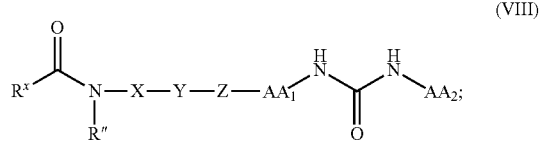

(VIII)

wherein

R" is H or optionally substituted alkyl;

$R^x$ is optionally substituted aryl or optionally substituted alkyl;

$AA_1$ and $AA_2$ are each independently a natural or unnatural amino acid;

X and Z are each independently $C_1$-$C_8$ alkyl, $C_2$-$C_8$ alkenyl, or $C_2$-$C_8$ alkynyl, $C_1$-$C_8$ heteroalkyl, $C_2$-$C_8$ heteroalkenyl, or $C_2$-$C_8$ heteroalkynyl, $C_1$-$C_8$ alkoxy, or a bond, each of which may be substituted with 0-5 $R_A$;

Y is —O—, —$S(O)_p$—, —NH—, —$NR_B$—, —CH=CH—, —$CR_B$=CH—, —CH=$CR_B$—, —NH—

CO—, —NH—CO$_2$—, —NR$_B$—CO—, —NR$_B$—CO$_2$—;
—CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl.

In another embodiment, the invention provides a compound of formula IX:

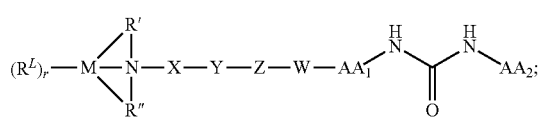

(IX)

wherein

M is a metal;

R$^L$ is a metal ligand;

R' is —CO—NR$^x$R$^y$—, —CS—NR$^x$R$^y$—, COR$^x$, CSR$^x$, C(NR$^x$)R$^x$, —S(O)$_p$R$^x$—, —CO$_2$—NR$^x$R$^y$—, or optionally substituted alkyl;

R" is H or optionally substituted alkyl;

R$^x$ is optionally substituted aryl or optionally substituted alkyl;

R$^y$ is H, optionally substituted aryl or optionally substituted alkyl;

X and Z are each independently C$_1$-C$_8$ alkyl, C$_2$-C$_8$ alkenyl, C$_2$-C$_8$ alkynyl, C$_1$-C$_8$ heteroalkyl, C$_2$-C$_8$ heteroalkenyl, C$_2$-C$_8$ heteroalkynyl, C$_1$-C$_8$ alkoxy, or a bond, each of which may be substituted with 0-5 R$_A$;

Y and W are each independently —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl and r is 1-5.

In another embodiment, the invention provides a compound of formula X:

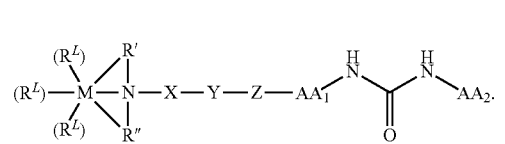

(X)

In one aspect, the invention provides a method of imaging in a subject, comprising the steps of:

providing a radiolabeled compound according to Formula IX:

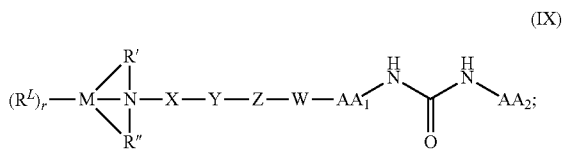

(IX)

wherein

M is a metal;

R$^L$ is a metal ligand;

R' is —CO—NR$^x$R$^y$—, —CS—NR$^x$R$^y$—, COR$^x$, CSR$^x$, C(NR$^x$)R$^x$, —S(O)$_p$R$^x$—, —CO$_2$—NR$^x$R$^y$—, or optionally substituted alkyl;

R" is H or optionally substituted alkyl;

R$^x$ is optionally substituted aryl or optionally substituted alkyl;

R$^y$ is H, optionally substituted aryl or optionally substituted alkyl;

X and Z are each independently C$_1$-C$_8$ alkyl, C$_2$-C$_8$ alkenyl, C$_2$-C$_8$ alkynyl, C$_1$-C$_8$ heteroalkyl, C$_2$-C$_8$ heteroalkenyl, C$_2$-C$_8$ heteroalkynyl, C$_1$-C$_8$ alkoxy, or a bond, each of which may be substituted with 0-5 R$_A$;

Y and W are each independently —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl; and r is 1-5;

wherein the compound of Formula IX comprises at least one radioisotope; or a pharmaceutically acceptable salt thereof;

contacting cells or tissues with the compound;

detecting the compound in the cells or tissue; and imaging the compound in the cells or tissue.

In another aspect, the invention provides a method for identifying a compound which modulates the activity of a prostate-specific membrane antigen (PSMA), the method comprising:

a) contacting PSMA with a radiolabeled compound of formula IX under conditions suitable for modulation of the activity of PSMA; and b) detecting modulation of the activity of PSMA by the compound;

wherein the compound is capable of interacting with a binding site of PSMA.

In another aspect, the invention provides a method of synthesizing a compound of formula II or formula IX.

DETAILED DESCRIPTION OF THE INVENTION

Figure 1:
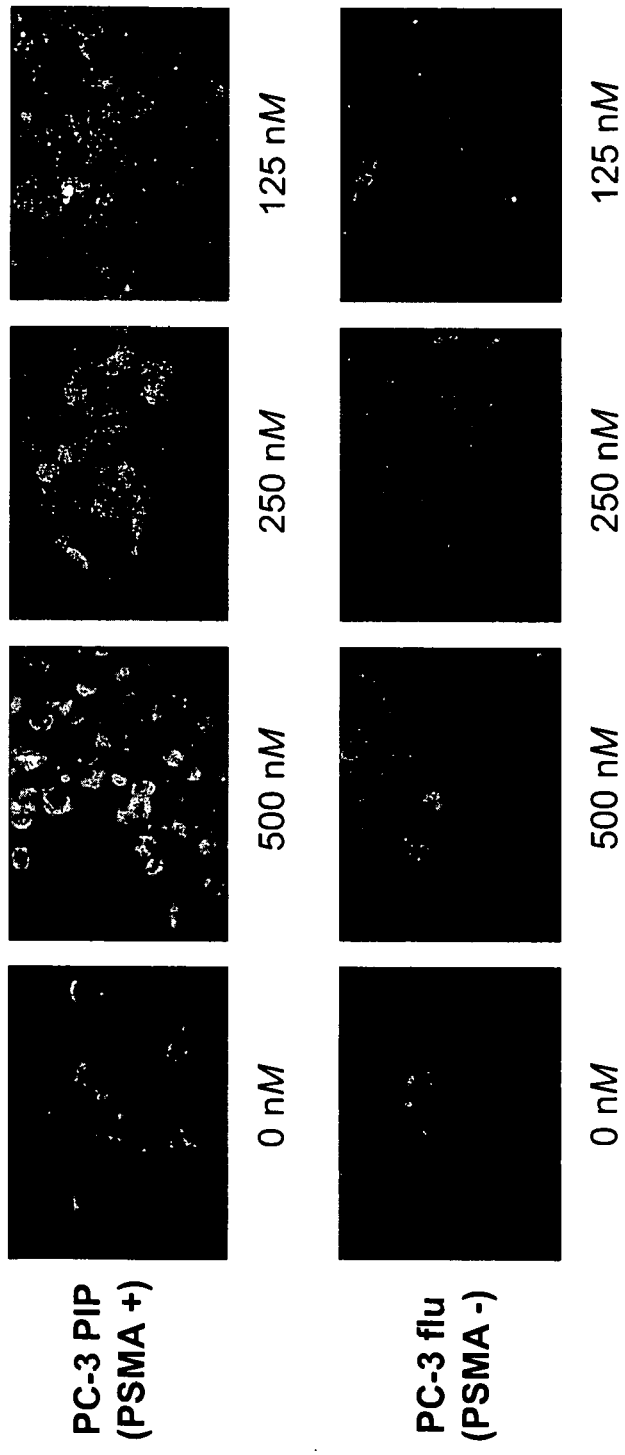
FIG. 1. Fluorescence microscopy of PSMA+ PC-3 PIP cells and PSMA− PC-3 flu cells using ReL2.

In one aspect, the invention provides a compound comprising an inhibitor, a linker, and a metal chelator.

In one embodiment, the inhibitor is an inhibitor of prostate specific membrane antigen (PSMA).

In another aspect, the invention provides a compound of formula I:

   (I);

wherein A is a metal chelator; B is a linker; C is a PSMA inhibitor; and b is 1-5.

In certain embodiments, the invention provides a compound of formula II:

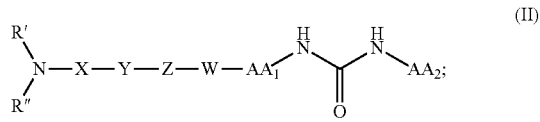   (II)

wherein

R' is —CO—NR$^x$R$^y$—, —CS$^x$R$^y$—, COR$^x$, CSR$^x$, C(NR$^x$)R$^x$, —S(O)$_p$R$^x$—, —CO$_2$—NR$^x$R$^y$—, or optionally substituted alkyl;

R" is H or optionally substituted alkyl;

R$^x$ is optionally substituted aryl or optionally substituted alkyl;

R$^y$ is H, optionally substituted aryl or optionally substituted alkyl;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y and W are each independently —O—, —S(O)$_p$—, —NH—, —NR$_B$—, —CH═CH—, —CR$_B$═CH—, —CH═CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

$R_A$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl.

In one embodiment, $AA_1$ and $AA_2$ are each independently a natural amino acid. In a further embodiment, $AA_1$ and $AA_2$ are each independently lysine, glutamic acid, tyrosine, or cysteine.

In another embodiment, R' is —CO—NR$^x$R$^y$—, —CS—NR$^x$R$^y$—, COR$^x$, CSR$^x$, or optionally substituted alkyl.

In still another embodiment, X is $C_1$-$C_8$ alkyl, $C_1$-$C_8$ alkoxy, or a bond, which may be substituted with 0-5 $R_A$; and $R_A$ for each occurrence, is halogen, hydroxy, amino, cyano, nitro, or $CO_2H$.

In certain embodiments, Z is $C_1$-$C_8$ alkyl, $C_1$-$C_8$ alkoxy, or a bond, which may be substituted with 0-5 $R_A$; and $R_A$ for each occurrence, is halogen, hydroxy, amino, cyano, nitro, or $CO_2H$.

In yet another embodiment, Y is —O—, —NH—, —NR$_B$—, —NH—CO—, —NH—CO$_2$—, —NR$_B$—CO—, —NR$_B$—CO$_2$—; —CO—NH—, —CO$_2$—NH—, —CO—NR$_B$—, or —CO$_2$—NR$_B$—. In a further embodiment, Y is —O—, —NH—CO— or —NR$_B$—CO—.

In other embodiments, the invention provides a compound of formula III:

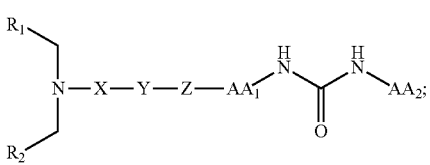

(III)

wherein

R$_1$ and R$_2$ are each independently selected from optionally substituted aryl, optionally substituted heteroaryl, optionally substituted heterocyclo, —COOH, hydroxyl, optionally substituted alkoxy, amino, optionally substituted mono or dialkylamino, thiol, and optionally substituted alkylthiol;

AA$_1$ and AA$_2$ are each independently a natural or unnatural amino acid;

X and Z are each independently C$_1$-C$_8$ alkyl, C$_2$-C$_8$ alkenyl, C$_2$-C$_8$ alkynyl, C$_1$-C$_8$ heteroalkyl, C$_2$-C$_8$ heteroalkenyl, C$_2$-C$_8$ heteroalkynyl, C$_1$-C$_8$ alkoxy, or a bond, each of which may be substituted with 0-5 R$_A$;

Y is —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl.

In a further embodiment, AA$_1$ and AA$_2$ are each independently a natural amino acid. In still another further embodiment, AA$_1$ and AA$_2$ are each independently lysine, glutamic acid, tyrosine, or cysteine.

In certain embodiments, R$_1$ is phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl, each of which is optionally mono-, di-, or tri-substituted with R$_C$; or R$_1$ is —COOH, hydroxyl, alkoxy, amino, mono or dialkylamino, and R$_C$ is halogen, hydroxy, amino, cyano, nitro, CO$_2$H, alkyl, alkoxy, mono or dialkylamino, aryl, or heteroaryl.

In another embodiment, R$_2$ is phenyl, 1-naphthyl, 2-naphthyl, pyridyl, pyrimidinyl, pyrazinyl, pyridizinyl, quinolinyl, thienyl, thiazolyl, oxazolyl, isoxazolyl, pyrrolyl, furanyl, isoquinolinyl, or triazolyl, each of which is optionally mono-, di-, or tri-substituted with R$_C$; or R$_2$ is —COOH, hydroxyl, alkoxy, amino, mono or dialkylamino, and R$_C$ is halogen, hydroxy, amino, cyano, nitro, CO$_2$H, alkyl, alkoxy, mono or dialkylamino, aryl, or heteroaryl.

In one embodiment, X is C$_1$-C$_8$ alkyl, C$_1$-C$_8$ alkoxy, or a bond, which may be substituted with 0-5 R$_A$; and R$_A$ for each occurrence, is halogen, hydroxy, amino, cyano, nitro, or CO$_2$H.

In another embodiment, Z is C$_1$-C$_8$ alkyl, C$_1$-C$_8$ alkoxy, or a bond, which may be substituted with 0-5 R$_A$; and R$_A$ for each occurrence, is halogen, hydroxy, amino, cyano, nitro, or CO$_2$H.

In still another embodiment, Y is —O—, —NH—, —NR$_B$—, —NH—CO—, —NH—CO$_2$—, —NR$_B$—CO—, —NR$_B$—CO$_2$—; —CO—NH—, —CO$_2$—NH—, —CO—NR$_B$—, or —CO$_2$—NR$_B$—; in certain instances, Y is —O—, —NH—CO— or —NR$_B$—CO—.

In certain embodiments, the invention provides a compound of formula IV:

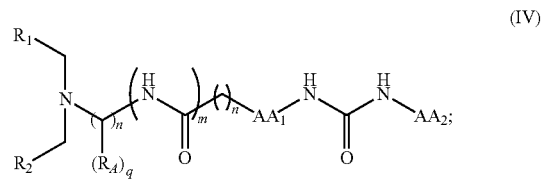

(IV)

wherein

AA$_1$ and AA$_2$ are each independently a natural amino acid;

R$_1$ is pyridyl, pyrimidinyl, pyrazinyl, pyridizinyl, quinolinyl, thienyl, thiazolyl, oxazolyl, isoxazolyl, pyrrolyl, furanyl, isoquinolinyl, imiazolyl, or triazolyl;

R$_2$ is pyridyl, pyrimidinyl, pyrazinyl, pyridizinyl, quinolinyl, thienyl, thiazolyl, oxazolyl, isoxazolyl, pyrrolyl, furanyl, isoquinolinyl, or triazolyl, —COOH, hydroxyl, alkoxy, amino, mono or dialkylamino;

R$_A$, for each occurrence, is halogen, hydroxy, amino, cyano, nitro, or CO$_2$H;

m is 0 or 1;

each n is independently 1-8; and each q is independently 0 or 1.

In one embodiment, AA$_1$ is lysine and AA$_2$ is glutamic acid or tyrosine. In a further embodiment, AA$_1$ is lysine and AA$_2$ is cysteine or tyrosine.

In certain embodiments, each n is independently 5-7. In other embodiments, m is 1.

In one embodiment, the invention provides for a compound of formula V:

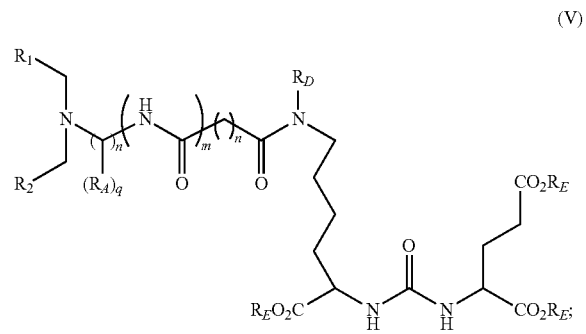

(V)

wherein each R$_D$ is independently H, optionally substituted alkyl, optionally substituted cycloalkyl, optionally substituted aryl, optionally substituted heteroaryl, optionally substituted heterocyclo, or optionally substituted aralkyl;

each R$_E$ is independently H, optionally substituted alkyl, optionally substituted cycloalkyl, optionally substituted aryl, optionally substituted heteroaryl, optionally substituted heterocyclo, or optionally substituted aralkyl;

$R_1$ is pyridyl, pyrimidinyl, pyrazinyl, pyridizinyl, isoquinolinyl, imiazolyl, or quinolinyl;

$R_2$ is pyridyl, pyrimidinyl, pyrazinyl, pyridizinyl, isoquinolinyl, quinolinyl; —COOH, hydroxyl, alkoxy, amino, mono or dialkylamino;

$R_4$, for each occurrence, is hydroxy, amino, or $CO_2H$;

each m is independently 0 or 1; and each n is independently 1-8.

In certain embodiments, $R_1$ is pyridyl, isoquinolinyl, imiazolyl, or quinolinyl. In other embodiments, $R_2$ is pyridyl, isoquinolinyl, quinolinyl, or —COOH.

In still another embodiment, each n is independently 5-7. In yet another embodiment, m is 1.

In certain embodiments, the invention provides a compound selected from the following:

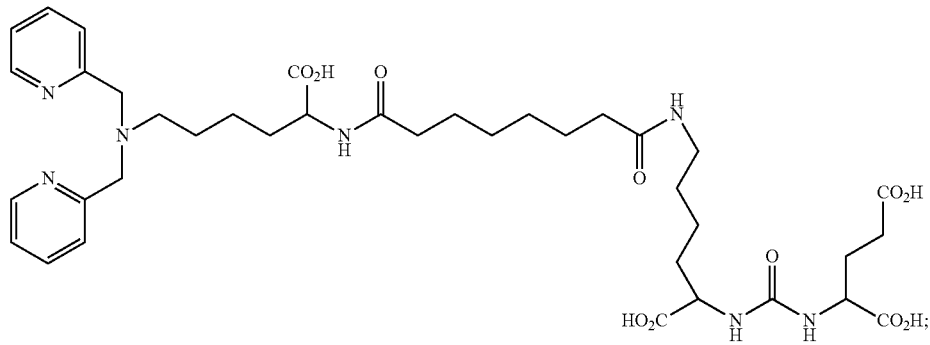

L1

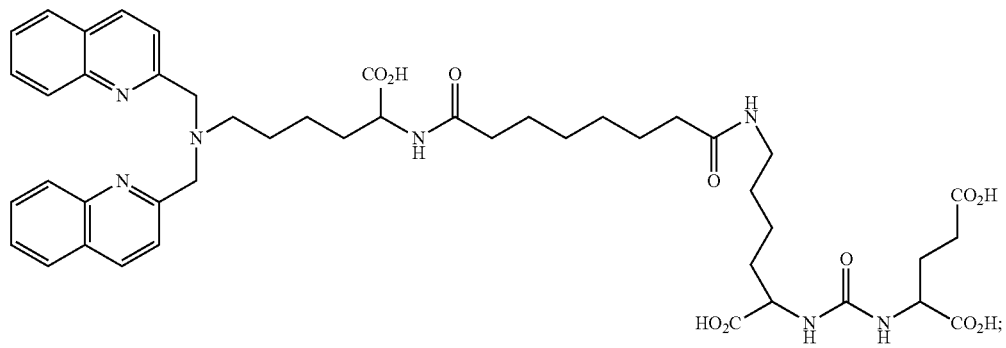

L2

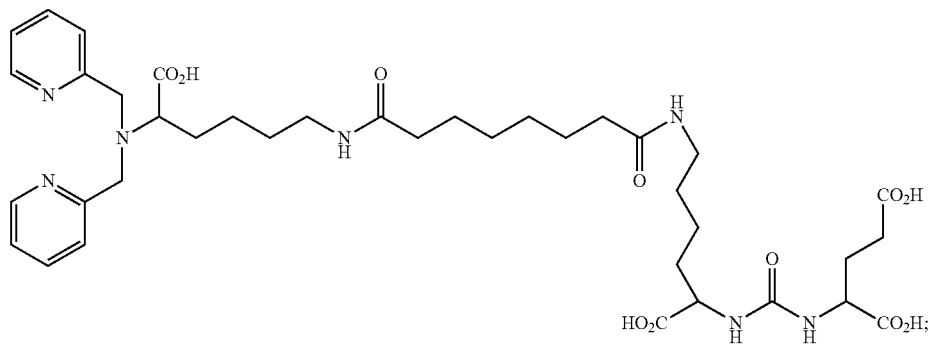

L3

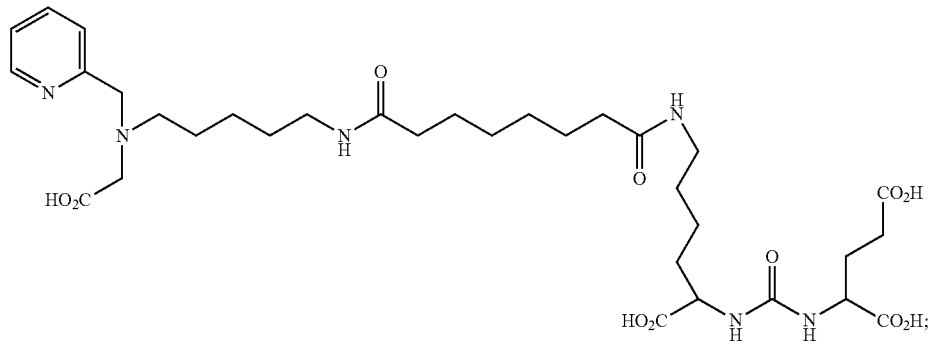

L4

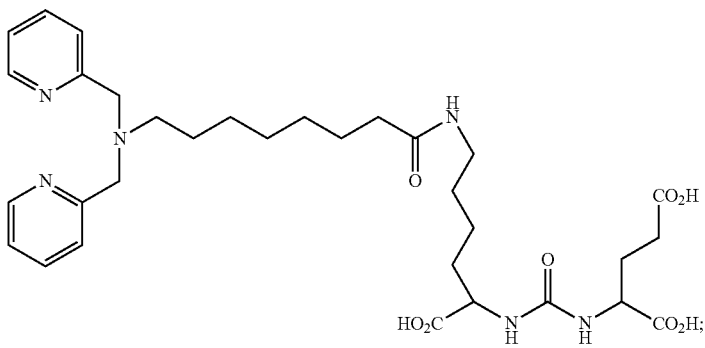

L5

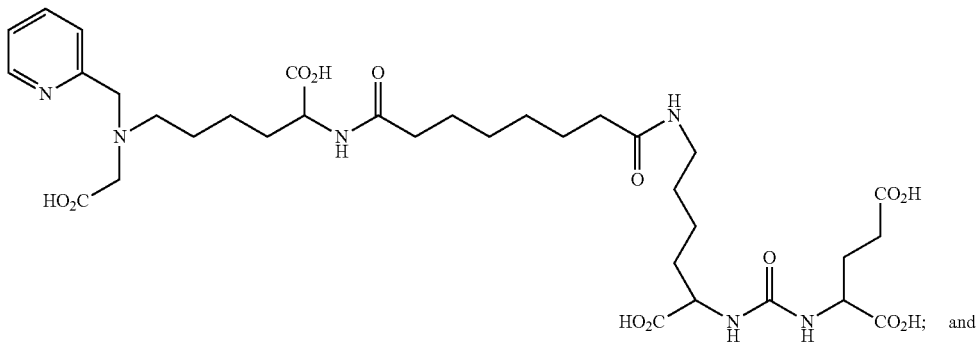

L6

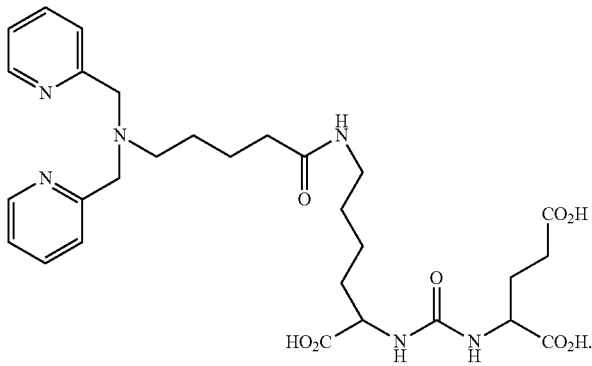

L7

In another embodiment, the invention provides a compound of formula VI:

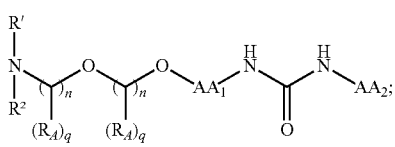

(VI)

wherein

AA$_1$ and AA$_2$ are each independently a natural amino acid;
R' is —CO—NR$^x$R$^y$—, —CS—NR$^x$R$^y$—, COR$^x$, CSR$^x$, C(NR$^x$)R$^x$, —S(O)$_p$R$^x$—, —CO$_2$—NR$^x$R$^y$—, or optionally substituted alkyl;
R" is H or optionally substituted alkyl;
R$^x$ is optionally substituted aryl or optionally substituted alkyl;
R$^y$ is H, optionally substituted aryl or optionally substituted alkyl;

R$_A$, for each occurrence, is halogen, hydroxy, amino, cyano, nitro, or CO$_2$H;
each n is independently 0-8; and
each q is independently 0 or 1.

In another embodiment, the invention provides a compound of formula VII:

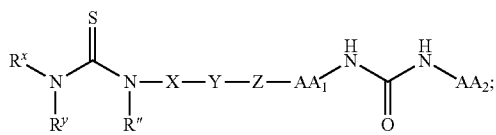

(VII)

wherein

R" is H or optionally substituted alkyl;
R$^x$ is optionally substituted aryl or optionally substituted alkyl;
R$^y$ is H, optionally substituted aryl or optionally substituted alkyl;

AA$_1$ and AA$_2$ are each independently a natural or unnatural amino acid;

X and Z are each independently C$_1$-C$_8$ alkyl, C$_2$-C$_8$ alkenyl, or C$_2$-C$_8$ alkynyl, C$_1$-C$_8$ heteroalkyl, C$_2$-C$_8$ heteroalkenyl, or C$_2$-C$_8$ heteroalkynyl, C$_1$-C$_8$ alkoxy, or a bond, each of which may be substituted with 0-5 R$_A$;

Y is —O—, —S(O)$_p$—, —NH—, —NR$_B$—, —CH=CH—, —CR$_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl.

In certain embodiments, R" and R$^y$ are H.

In other embodiments, R$^x$ is optionally substituted aryl.

In another embodiment, aryl is substituted with optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl, optionally substituted alkyl-heterocyclo; or optionally substituted alkyl-heteroaryl.

In a further embodiment, aryl is substituted with optionally substituted alkyl-heterocyclo or optionally substituted alkyl-heteroaryl.

In still another embodiment, aryl is substituted with

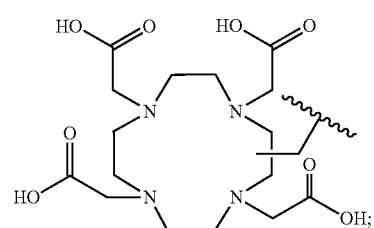

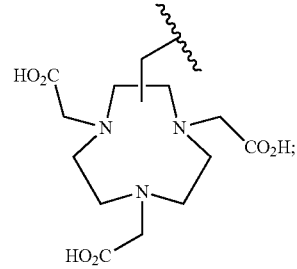

-continued

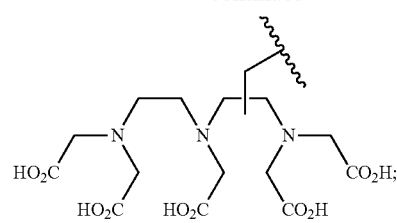

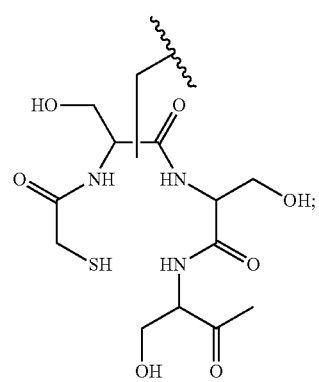

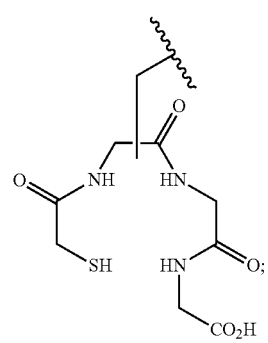

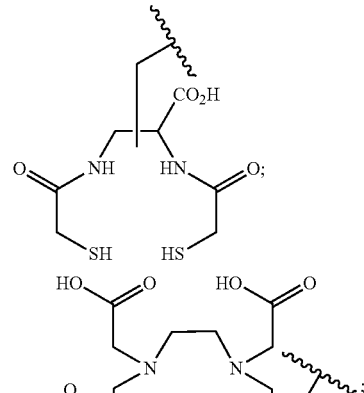

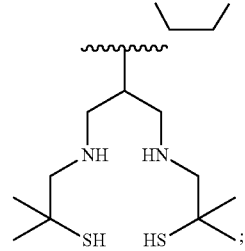

-continued

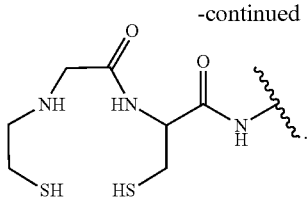

In one embodiment, the invention provides a compound of formula VIII:

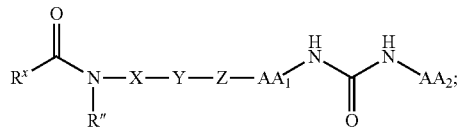

(VIII)

wherein

R″ is H or optionally substituted alkyl;

$R^x$ is optionally substituted aryl or optionally substituted alkyl;

$AA_1$ and $AA_2$ are each independently a natural or unnatural amino acid;

X and Z are each independently $C_1$-$C_8$ alkyl, $C_2$-$C_8$ alkenyl, or $C_2$-$C_8$ alkynyl, $C_1$-$C_8$ heteroalkyl, $C_2$-$C_8$ heteroalkenyl, or $C_2$-$C_8$ heteroalkynyl, $C_1$-$C_8$ alkoxy, or a bond, each of which may be substituted with 0-5 $R_4$;

Y is —O—, —S(O)$_p$—, —NH—, —NR$_B$—, —CH═CH—, —CR$_B$═CH—, —CH═CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

$R_4$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl.

In one embodiment, R″ is H.

In another embodiment, $R^x$ is optionally substituted alkyl. In a further embodiment, alkyl is substituted with optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl, optionally substituted alkyl-heterocyclo; or optionally substituted alkyl-heteroaryl. In a further embodiment, alkyl is substituted with optionally substituted heterocyclo or optionally substituted heteroaryl.

In certain embodiments, alkyl is substituted with

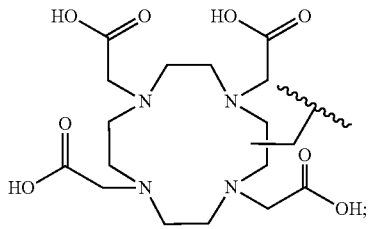

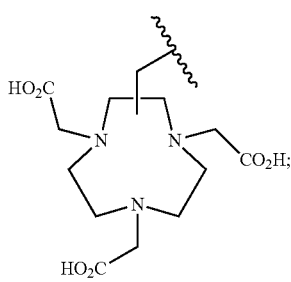

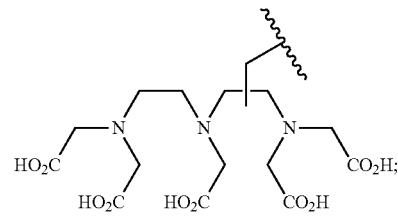

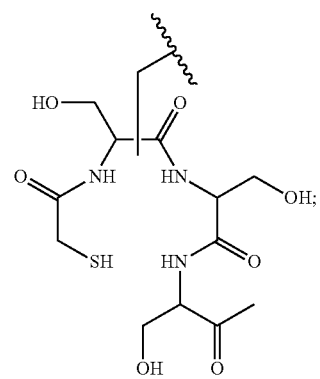

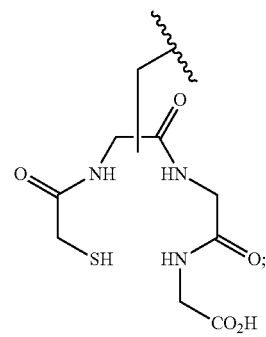

21
-continued
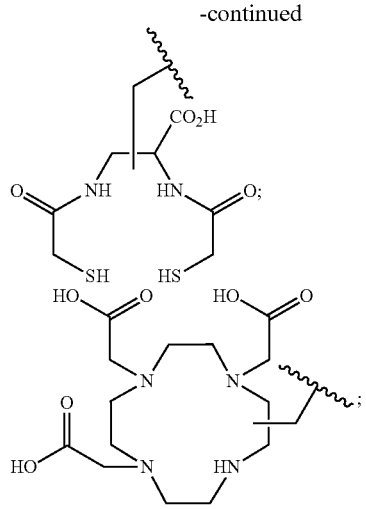
22
-continued
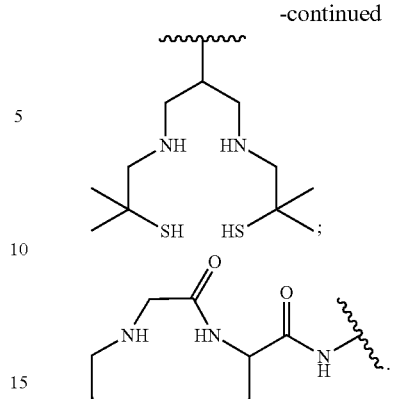
In certain embodiments, the invention provides for the following compounds:
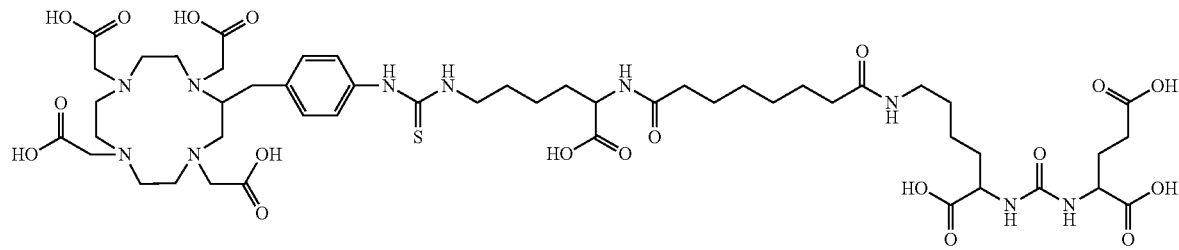
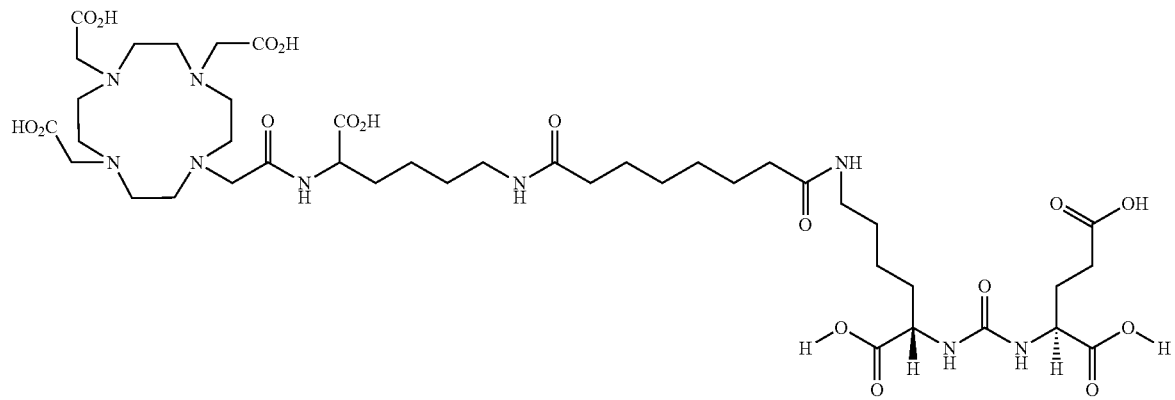
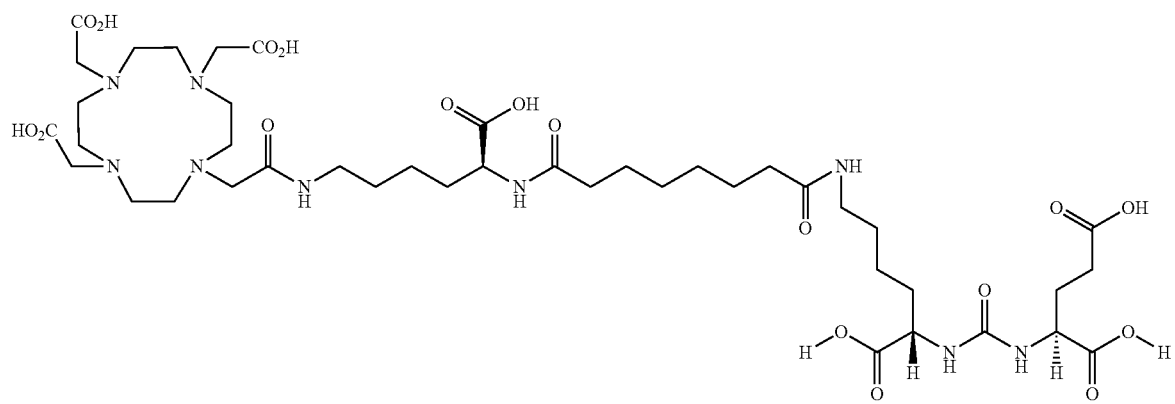

In another embodiment, the invention provides a compound further comprising a metal.

In another embodiment, the invention provides a compound of formula IX:

$$(R^L)_r—M\begin{smallmatrix}R'\\|\\N\\|\\R''\end{smallmatrix}—X—Y—Z—W—AA_1\overset{H}{N}\underset{O}{\overset{\|}{C}}\overset{H}{N}AA_2; \quad (IX)$$

wherein

M is a metal;

$R^L$ is a metal ligand;

R' is —CO—$NR^xR^y$—, —CS—$NR^xR^y$—, $COR^x$, $CSR^x$, $C(NR^x)R^x$, —$S(O)_pR^x$—, —$CO_2$—$NR^xR^y$—, or optionally substituted alkyl;

R" is H or optionally substituted alkyl;

$R^x$ is optionally substituted aryl or optionally substituted alkyl;

$R^y$ is H, optionally substituted aryl or optionally substituted alkyl;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y and W are each independently —O—, —$S(O)_p$—, —NH—, —$NR_B$—, —CH=CH—, —$CR_B$=CH—, —CH=$CR_B$—, —NH—CO—, —NH—$CO_2$—, —$NR_B$—CO—, —$NR_B$—$CO_2$—; —CO—NH—, —$CO_2$—NH—, —CO—$NR_B$—, —$CO_2$—$NR_B$—, or a bond;

p is 0, 1, or 2;

$R_A$, for each occurrence, is halogen, hydroxy, amino, cyano, nitro, $CO_2H$, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and $R_B$, for each occurrence, is optionally substituted alkyl, optionally substituted alkoxy, optionally substituted mono or dialkylamino, optionally substituted alkylthio, optionally substituted aryl, or optionally substituted heteroaryl and r is 1-5.

In certain embodiments, M is Tc, Re, Ga, Cu, Y, Ac, Bi or In. In a further embodiment, the metal is a radioactive isotope. In still another further embodiment, M is Tc-99m, Re-188, Re-186, Ga-68, Cu-64, Y-90, Y-86, Ac-225, Bi-213, In-111, Tc-94m, Sm-153, Ho-166, Lu-177, Cu-67, or Dy-166.

In another embodiment, R' is CO.

In still another embodiment, r is 1-3.

In another embodiment, the invention provides a compound of formula X:

$$(R^L)\begin{smallmatrix}\\(R^L)—M\\(R^L)\end{smallmatrix}\begin{smallmatrix}R'\\|\\N\\|\\R''\end{smallmatrix}—X—Y—Z—AA_1\overset{H}{N}\underset{O}{\overset{\|}{C}}\overset{H}{N}AA_2;. \quad (X)$$

In one aspect, the invention provides a method of imaging in a subject, comprising the steps of:

providing a radiolabeled compound according to Formula IX:

$$(R^L)_r—M\begin{smallmatrix}R'\\|\\N\\|\\R''\end{smallmatrix}—X—Y—Z—W—AA_1\overset{H}{N}\underset{O}{\overset{\|}{C}}\overset{H}{N}AA_2; \quad (IX)$$

wherein

M is a metal;

$R^L$ is a metal ligand;

R' is —CO—$NR^xR^y$—, —CS—$NR^xR^y$—, $COR^x$, $CSR^x$, $C(NR^x)R^x$, —$S(O)_pR^x$—, —$CO_2$—$NR^xR^y$—, or optionally substituted alkyl;

R" is H or optionally substituted alkyl;

$R^x$ is optionally substituted aryl or optionally substituted alkyl;

$R^y$ is H, optionally substituted aryl or optionally substituted alkyl;

X and Z are each independently $C_1$-$C_8$ alkyl, $C_2$-$C_8$ alkenyl, $C_2$-$C_8$ alkynyl, $C_1$-$C_8$ heteroalkyl, $C_2$-$C_8$ heteroalkenyl, $C_2$-$C_8$ heteroalkynyl, $C_1$-$C_8$ alkoxy, or a bond, each of which may be substituted with 0-5 $R_A$;

Y and W are each independently —O—, —$S(O)_p$—, —NH—, —$NR_B$—, —CH=CH—, —$CR_B$=CH—, —CH=CR$_B$—, —NH—CO—, —NH—CO$_2$—, —NR$_B$—CO—, —NR$_B$—CO$_2$—; —CO—NH—, —CO$_2$—NH—, —CO—NR$_B$—, —CO$_2$—NR$_B$—, or a bond;

p is 0, 1, or 2;

R$_A$, for each occurrence, is halogen, hydroxy, amino, cyano, nitro, CO$_2$H, optionally substituted alkyl, optionally substituted cycloalkyl, optionally substituted heterocyclo, optionally substituted alkenyl, optionally substituted alkynyl, optionally substituted alkoxy, optionally substituted mono or dialkylamino, optionally substituted alkylthio, optionally substituted alkylsulfinyl, optionally substituted alkylsulfonyl, optionally substituted mono- or dialkylcarboxamide, optionally substituted aryl, or optionally substituted heteroaryl; and R$_B$, for each occurrence, is optionally substituted alkyl, optionally substituted alkoxy, optionally substituted mono or dialkylamino, optionally substituted alkylthio, optionally substituted aryl, or optionally substituted heteroaryl; and r is 1-5;

wherein the compound of Formula IX comprises at least one radioisotope; or a pharmaceutically acceptable salt thereof;

contacting cells or tissues with the compound;

detecting the compound in the cells or tissue; and imaging the compound in the cells or tissue.

In one embodiment, the invention provides a method wherein the metal is Tc-99m, Re-188, Re-186, Ga-68, Cu-64, Y-90, Y-86, Ac-225, Bi-213, In-111, Tc-94m, Sm-153, Ho-166, Lu-177, Cu-67, or Dy-166.

In another embodiment, the imaging method is suitable for imaging PSMA inhibitors.

In still another embodiment, the imaging method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer (e.g., gliomas), throat cancer, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In certain embodiments, the radiolabeled compound is stable in vivo.

In other embodiments, the radiolabeled compound is detected by positron emission tomography (PET) or single photon emission computed tomography (SPECT).

In one embodiment, the invention provides a method wherein the subject is a human, rat, mouse, cat, dog, horse, sheep, cow, monkey, avian, or amphibian.

In another embodiment, the cell is in vivo or in vitro.

In another aspect, the invention provides a method for identifying a compound which modulates the activity of a prostate-specific membrane antigen (PSMA), the method comprising:

a) contacting PSMA with a radiolabeled compound of formula IX under conditions suitable for modulation of the activity of PSMA; and b) detecting modulation of the activity of PSMA by the compound;

wherein the compound is capable of interacting with a binding site of PSMA.

In one embodiment, the modulation is inhibition.

In another embodiment, the binding site comprises a binuclear zinc ion and two substrate binding pockets.

In still another embodiment, the modulation of the activity of PSMA is detected by use of an assay for deacetylation activity.

In certain embodiments, the PSMA inhibitor has an IC$_{50}$ value ranging from about 0.1 to about 200 nM. In a further embodiment, the PSMA inhibitor has an IC$_{50}$ value ranging from about 0.5 to about 118 nM.

In another aspect, the invention provides a method of synthesizing a compound of formula II or formula IX.

In certain instances, an amino acid moiety of a compound of the invention is connected to a linker moiety of a compound of the invention. In certain instances, an amino acid (AA), is connected to a functional group Z or W. In one embodiment, the amino acid is connected to Z or W by a bond. In certain embodiments, the amino acid is connected to Z or W by a functional group selected from a divalent alkyl group (alkylene), alkene, alkyne, ether, thio ether, amine, mono-substituted amine, carbonyl, ester, amide, urea, carbamate, and carbonate.

In certain embodiments, a compound of the invention comprises at least one radioactive isotope.

Certain preferred compounds of the invention include those comprising at least one radioactive isotope or more preferably one or more positron emitting radioactive isotopes. In certain embodiments, the invention provides compounds comprising one or more radioisotope suitable for use in radiation therapy In certain embodiments, the compounds of the invention comprise at least one radioactive isotope of technetium, rhenium, gallium, indium, copper, yttrium, actinium, bismuth, samarium, dysprosium, holmium, or lutetium, including radioactive isotopes selected from Tc-99m, Tc-94m, Re-186, Re-188, Ga-68, Cu-64, Cu-67, Y-90, Y-86, Ac-225, Bi-213, In-111, Sm-153, Ho-166, Lu-177, and Dy-166.

Various compounds of the invention, particularly compounds suitable for use in the imaging methods provided by the invention, include one or more radioisotopes capable of emitting one or more forms of radiation which are suitable for detection with any standard radiology equipment such as PET, SPECT, gamma cameras, MRI and the like.

Preferred imaging methods provided by the invention include the use of compounds of the invention which are capable of generating at least a 2:1 target to background ratio of radiation intensity, or more preferably about a 5:1, about a 10:1 or about a 15:1 ratio of radiation intensity between target and background.

In preferred methods of the invention the compounds of the invention are excreted from tissues of the body quickly to prevent prolonged exposure to the radiation of the radiolabeled compound administered to the patient. Typically compounds of the invention are eliminated from the body in less than about 24 hours. More preferably, compounds of the invention are eliminated from the body in less than about 16 hours, 12 hours, 8 hours, 6 hours, 4 hours, 2 hours, 90 minutes, or 60 minutes. Typically preferred compounds are eliminated in between about 60 minutes and about 120 minutes.

Preferred compounds of the invention are stable in vivo such that substantially all, e.g., more than about 50%, 60%, 70%, 80%, or more preferably 90% of the injected compound is not metabolized by the body prior to excretion.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

The present invention also provide packaged pharmaceutical compositions comprising a pharmaceutical acceptable carrier and a compound of the invention. In certain embodiments the packaged pharmaceutical composition will comprise the reaction precursors necessary generate the compound of the invention upon combination with a radiolabeled precursor.

In certain preferred embodiments, the invention provides a kit according to the invention contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

The kit may provide a compound of the invention in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the targeting molecule/chelating agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment are optimized in accordance with the methods for making the cardiovascular imaging agent set forth above. Radionuclides, including, but not limited to, $^{99m}$Tc obtained from a commercially available $^{99}$Mo/$^{99m}$Tc generator, may be combined with the unlabeled targeting molecule/chelating agent and the reducing agent for a time and at a temperature sufficient to chelate the radionuclide to the targeting molecule/chelating agent, and the imaging agent thus formed is injected into the patient.

Imaging agents of the invention may be used in accordance with the methods of the invention by one of skill in the art. Images can be generated by virtue of differences in the spatial distribution of the imaging agents which accumulate at a site when contacted with PSMA. The spatial distribution may be measured using any means suitable for the particular label, for example, a gamma camera, a PET apparatus, a SPECT apparatus, and the like. The extent of accumulation of the imaging agent may be quantified using known methods for quantifying radioactive emissions. A particularly useful imaging approach employs more than one imaging agent to perform simultaneous studies.

Preferably, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

Structure-Based Design of PSMA Binding Inhibitors.

The binding site of PSMA contains a binuclear zinc ion and two substrate binding pockets, i.e., an S1 (nonpharmacophore) pocket and an S1' (pharmacophore) pocket. The active site also contains a chloride ion in the S1 pocket. In the vicinity of the S1 pocket resides a funnel-shaped tunnel with a depth of approximately 20 Å and a width of 8-9 Å. Similarly, a narrow cavity is present near the S1' pocket. Moreover, it has been determined that the glutamate moiety of the inhibitors has a predisposition to orient within the narrow S1' pocket, whereas the remainder of the molecule resides within the large S1 pocket. These observations are similar for PSMA X-ray crystal structures upon co-crystallization with compounds in the urea series, namely, DCMC, DCIT and DCFBC. It was desired to synthesize a conjugate between a glutamate-containing, urea-based inhibitor and known chelators of [Re(I)(CO)$_3$]$^+$/[$^{99m}$Tc(I)(CO)$_3$]$^+$. In the design of these new conjugates, it was important to optimize the interaction between PSMA and the bulky chelator. Considering the ~9 Å diameter of the rhenium tricarbonyl and technetium tricarbonyl coordination spheres with pyridyl-based chelates, determined from reported X-ray crystal structures, the calculated average volume of the metal tricarbonyl core with the bispyridyl chelate was found to be ~378 Å. To enable high-affinity binding of the putative imaging agents to PSMA, a with 4-methoxybenzyl chloride and cesium carbonate in N,N-dimethylformamide (DMF), followed by removal of the Fmoc group using 20% piperidine in DMF. Flash chromatography provided the desired compound 2 in 80% yield. Urea 3 was obtained by treating Bis-4-methoxybenzyl-L-glutamate-.HCl, 4 with triphosgene and triethylamine at −78° C. followed by in situ trapping of the isocyanate intermediate by addition of 2. Selective cleavage of the N-Boc group of 3 with p-toluenesulfonic acid in ethanol/ethyl acetate produced 5. Basic extraction of a solution of 5 in CH$_2$Cl$_2$ gave the free base 1. The p-methoxybenzyl (PMB) group was conveniently removed at room temperature by using trifluoroacetic acid (TFA)/anisole or TFA/CH$_2$Cl$_2$ solution in the final step after performing the required conjugation.

Scheme 1

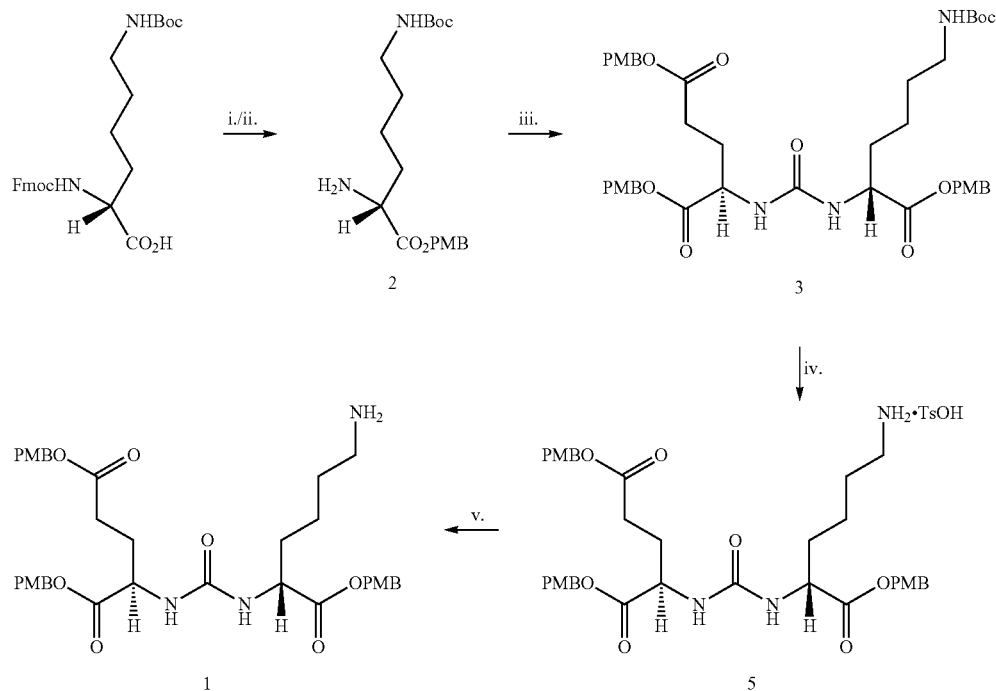

PMB = p-methoxy benzyl group; i. 4-methoxybenzyl chloride, Cs$_2$CO$_3$, DMF, rt, 4 h; ii. 20% piperidine, DMF, rt, 20 min; iii. 4, Triphosgene, NEt$_3$, CH$_2$Cl$_2$, -80° C. to rt; iv. TsOH Ethanol, ethyl acetate, rt, 2 h; v. 0.5 (N) NaHCO$_3$.

methylene linker (>20 Å) was attached to the remainder of the molecule from the α-carbon of the urea function. Accordingly, three sets of compounds, each with a different linker length: L1-L3, with a linker of ~31.5 Å; L4 and L7 with linker length of ~33 Å; and L5 and L6, with linker lengths of ~22 Å and 7.7 Å, respectively, were synthesized.

Synthesis of Urea-Linked Chelators.

A series of PSMA inhibitors containing lysine was developed in order to utilize the free ε amine of lysine for conjugation or derivatization with a suitable metal chelating group. Compound 1 (Scheme 1) is a key intermediate, integral to synthesis of all of the putative imaging agents described. The protected lysine analog 2 was prepared in two steps. Commercially available N$_\epsilon$-Boc-N$_\alpha$Fmoc-L-lysine was reacted The synthesis of the chelators and their conjugation with intermediate 1 are presented in Schemes 2-6. Compound 1 was used to attach different linkers as well as metal chelators to generate a new series of PSMA inhibitors, L1-L7, for coordination of {$^{99m}$Tc(CO)$_3$}$^+$/{Re(CO)$_3$}$^+$. Key N-hydroxysuccinimide (NHS) ester intermediate 6, shown in Scheme 2, was prepared by conjugation of 1 with excess disuccinimidyl suberate (DSS) in DMF. Compound 6 was then reacted with three different bispyridyl chelators, 7, 9 and 13, a bisquinoline chelator, 8, and a monopyridyl monoacid chelator, 11, to prepare L1-L4, and L7. Chelators 7, 8, 9 and 13 were prepared according to published procedures (see Examples).

Scheme 2

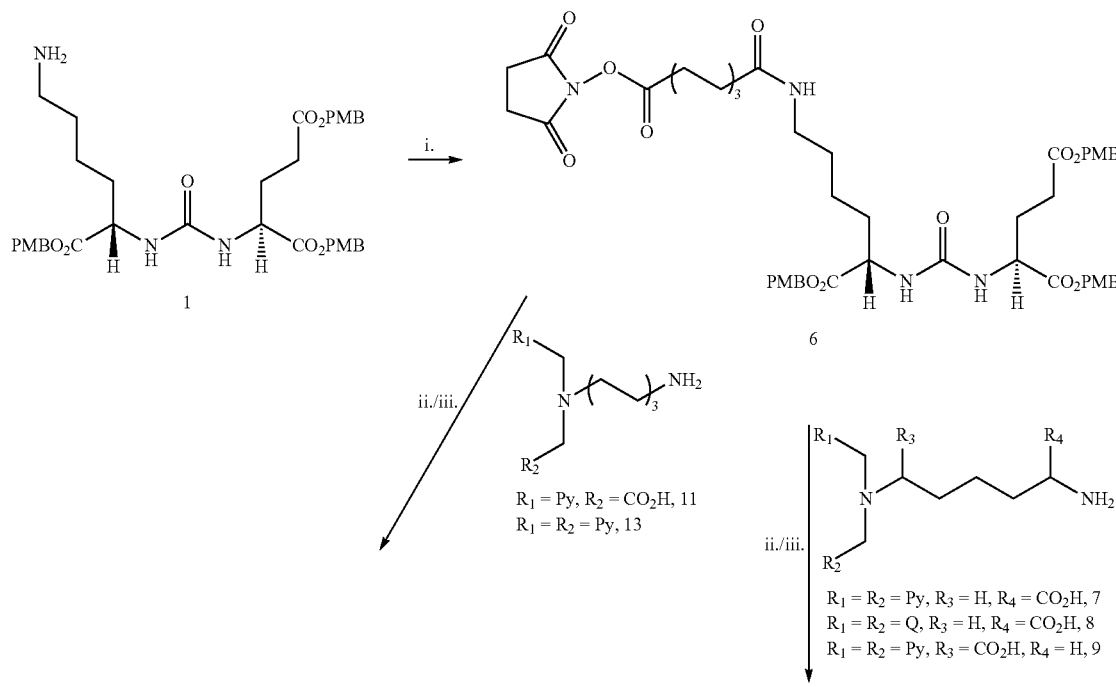

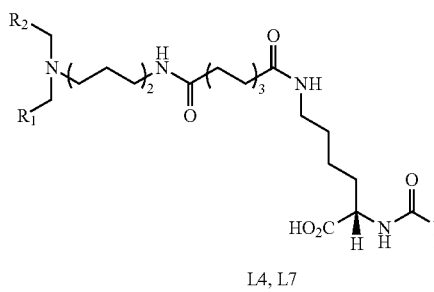

L4, L7

R₁ = Py, R₂ = CO₂H, L4
R₁ = R₂ = Py, L7

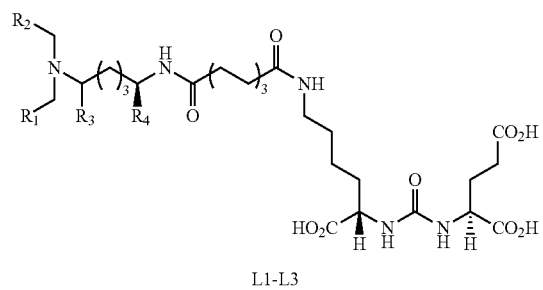

L1-L3

R₁ = R₂ = Py, R₃ = H, R₄ = CO₂H, L1
R₁ = R₂ = Q, R₃ = H, R₄ = CO₂H, L2
R₁ = R₂ = Py, R₃ = CO₂H, R₄ = H, L3 i. DSS, DMF, rt, 2 h; ii. NEt₃, DMF, rt, 8 h;
iii. TFA, anisole, rt, 20 min or TFA, CH₂Cl₂, rt, 4 h.

Synthesis of the monopyridyl monoacid chelator was performed by modification of a previously described procedure (Scheme 3). Compound 10 was prepared according to a previously reported method (see Examples). Reductive amination of 10, using glyoxylic acid in presence of sodium triacetoxyborohydride in dichloroethane, followed by removal of the protecting group using a solution of TFA/CH₂Cl₂ at ambient temperature, produced 11.

Scheme 3

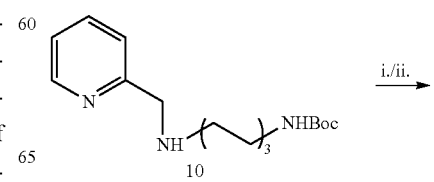

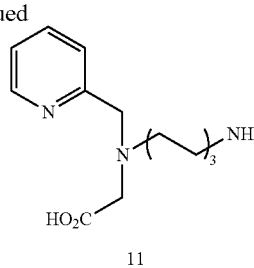

11 i. glyoxylic acid, NaBH(OAc)₃, CH₂Cl₂, rt, 16 h;
ii. TFA, CH₂Cl₂, rt, 4 h.

The synthesis of L5 is outlined in Scheme 4. Compound 12 was prepared by reductive amination of commercially available 8-aminocaproic acid with pyridine-2-carboxaldehyde and sodium triacetoxyborohydride followed by NHS ester formation with N-hydroxysuccinimide in presence of O-benzotriazole-N,N,N',N'-tetramethyluronium-hexafluoro-phosphate (HBTU). Compound L5 was obtained by reacting 12 with 5 in CH₂Cl₂ and triethylamine followed by deprotection of the PMB groups using TFA/CH₂Cl₂. Compound L6 was prepared by reductive amination of 1 using pyridine-2-carboxaldehyde and sodium triacetoxyborohydride followed by deprotection of the PMB groups using TFA/CH₂Cl₂ (Scheme 5).

Scheme 4

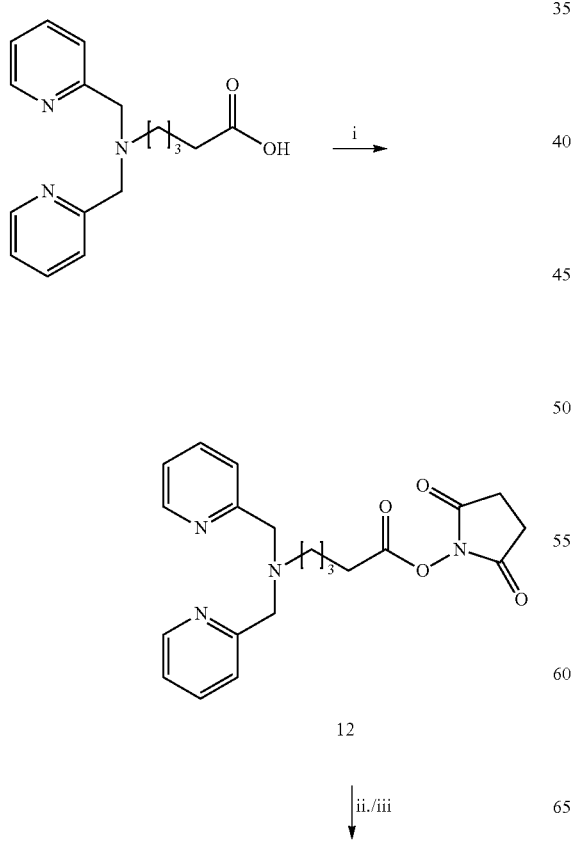

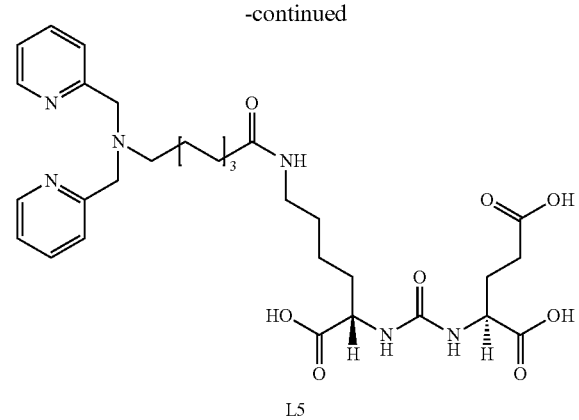

L5 i. N-hydroxysuccinimide, HBTU, DMF, 16 h;
ii. 5, NEt₃, CH₂Cl₂; iii. TFA, CH₂Cl₂, 4 h, 73%.

Scheme 5

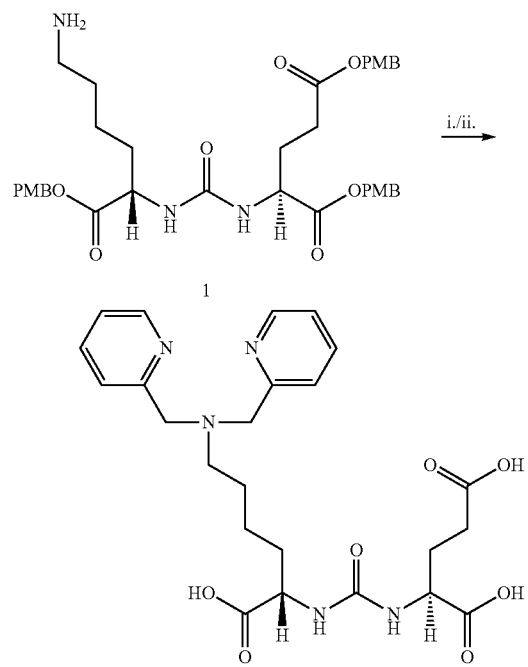

L6 i. pyridine-2-carboxaldehyde, NaBH(OAc)₃, CH₂Cl₂, rt, 4 h;
ii. TFA, CH₂Cl₂, rt, 2 h.

Synthesis of Rhenium Analogs (ReL1-ReL7).

Synthesis of compounds $[Re(CO)_3L]^{+/0}$ (L=L1-L7) was performed by ligand exchange reaction using the rhenium tricarbonyl precursor $[Re(CO)_3(H_2O)_3]Br^{37}$ as shown in Scheme 6 for L1. Equimolar quantities of the ligand (L1-L7) and the precursor were refluxed under argon for 3 h to afford the corresponding rhenium complex in quantitative yield in each case. The complexation was monitored by high-performance liquid chromatography (HPLC). All complexes were purified via HPLC and characterized by standard spectroscopic methods.

Scheme 6

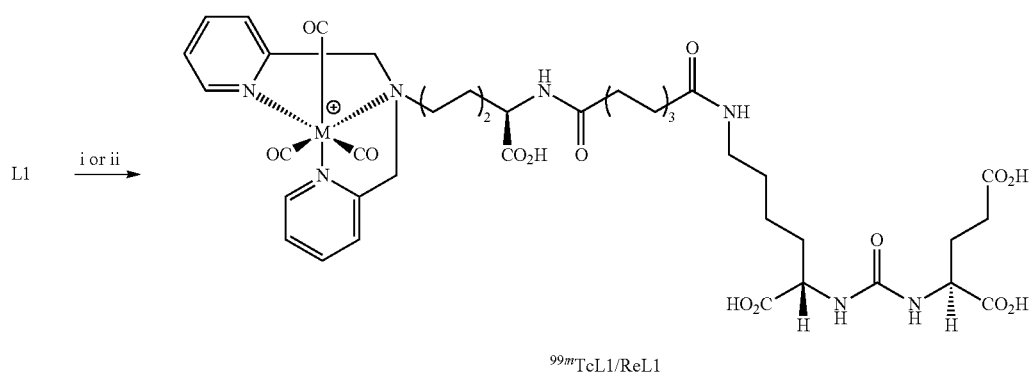

$^{99m}$TcL1/ReL1 i. [Tc(CO)$_3$(H$_2$O)$_3$]$^+$, pH 7.2, 95° C., 30 min;
ii. [NEt$_4$]$_2$[ReBr$_3$(CO)$_3$], 90° C., 4 h.

Synthesis of DOTA Analogs

All DOTA-L compounds were prepared by using same general procedure as shown in the scheme 7. A chain elongation agent was added to a stirred solution of a starting material substrate. Various groups on the newly formed substrate were deprotected, which was then followed by reaction with a DOTA agent. The DOTA compounds were then subject to labeling with a radioactive metal to provide the desired compound (Scheme 7).

Scheme 7

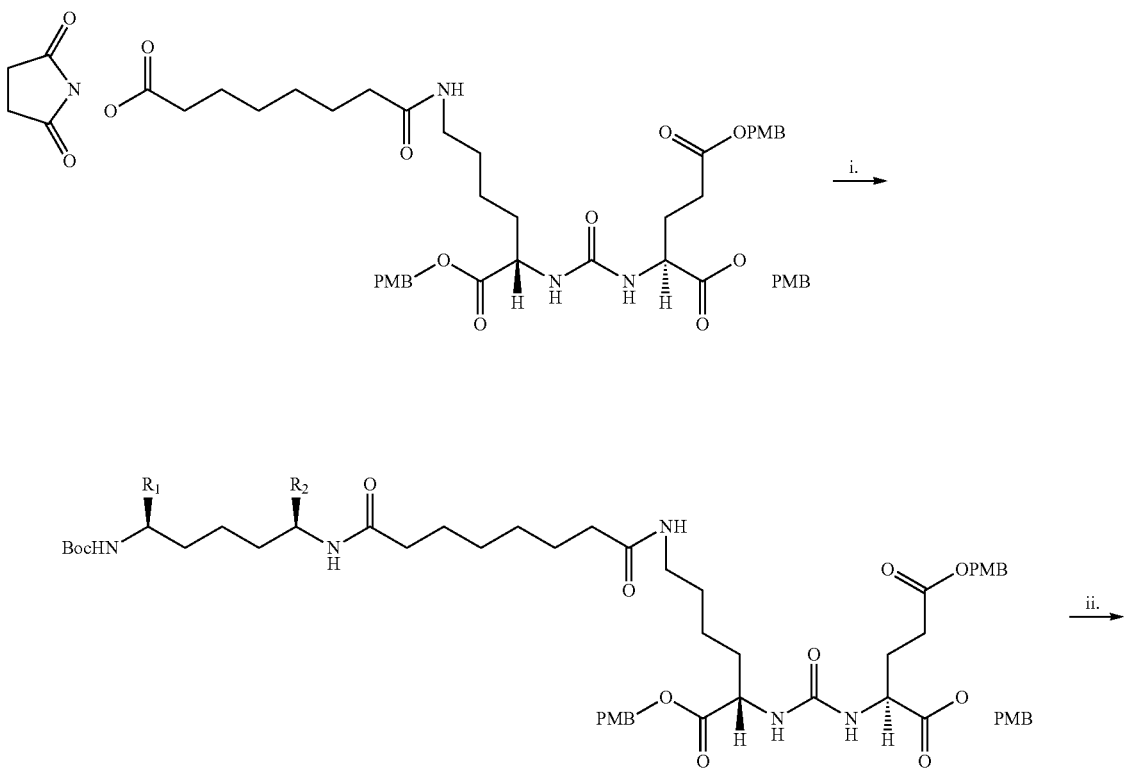

R$_1$ = H, R$_2$ = CO$_2$tBu, 14
R$_1$ = CO$_2$tBu, R$_2$ = H, 15

-continued

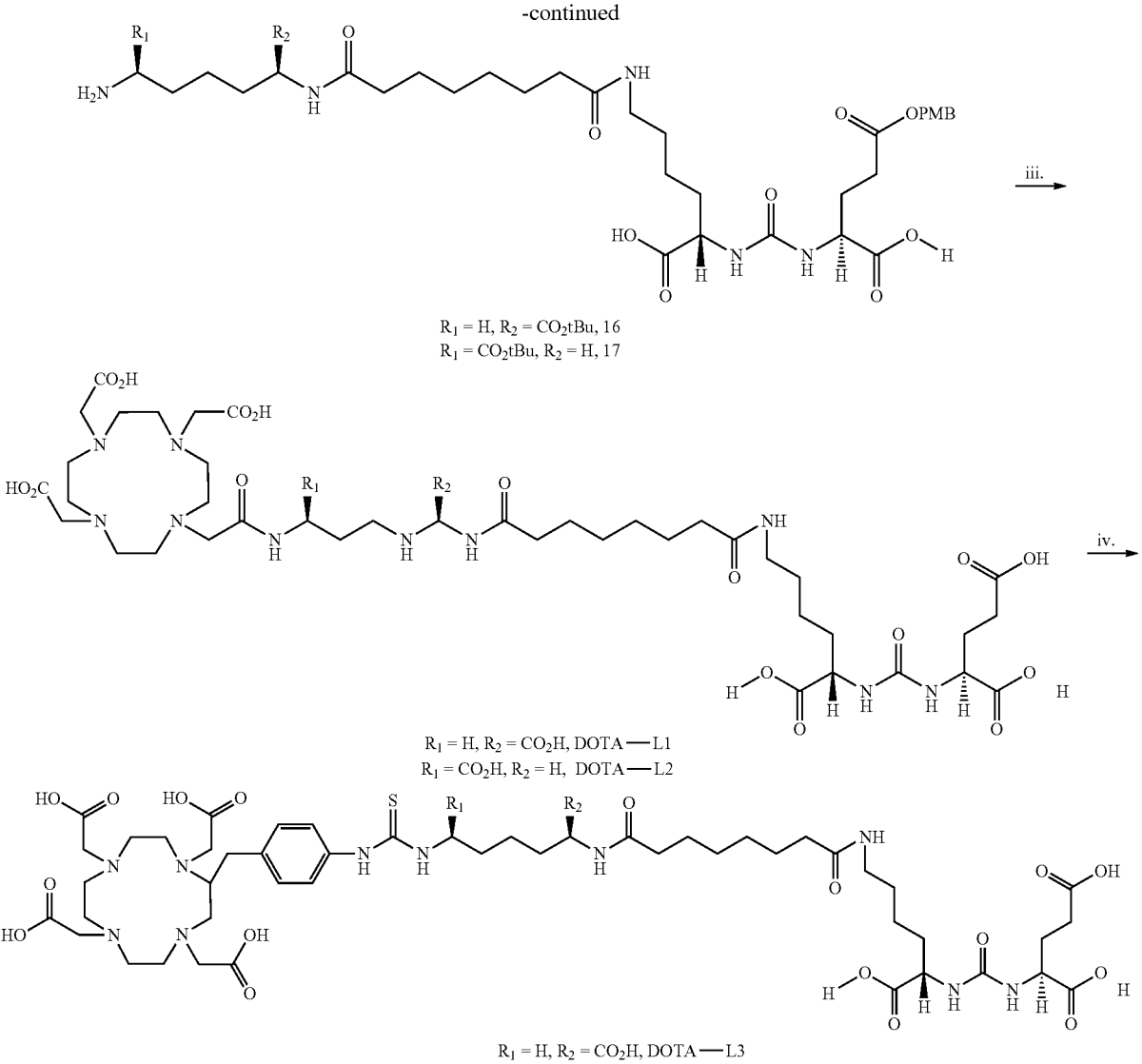

i. H-Lys(Boc)-OtBu or Boc-Lys-OtBu, DMF, NEt₃, rt, 16 hr;
ii. TFA/CH₂Cl, rt, 1 h;
iii. DOTA—NHA, pH = 7.2, PBS buffer, 3 h, rt;
iv. DOTA—Bz—NCS, pH = 9, borate buffer, 1 h, 50° C.

Modeling of L1 in the Active Site of PSMA.

For molecular modeling studies of L1 with PSMA, a recently published crystal structure of PSMA in complex with (S)-2-(4-iodobenzylphosphonomethyl)-pentanedioic acid (GPI-18431) (PDB ID: 2C6C) was used (Mesters, J. R.; et al. *Embo J* 2006, 25, 1375-1384). Initially, docking studies were carried out with L1 with the active site of 2C6C using LigandFit and CHARMm-based CDOCKER protocols implemented in Discovery Studio 1.7 (DS 1.7, Accelrys Inc.). However, none of them produced docked poses in the active site because of the bulkiness of L1. Therefore, an alternative way to elucidate a potential binding mode of L1 was employed. PSMA crystal structures with several ligands including GPI-18431, 2-(phosphonomethyl)pentanedioic acid (2-PMPA) and glutamate showed that the glutamate portion of these compounds within the S1'-pocket virtually overlap, suggesting that the orientation of the glutamate moiety is unchanged despite a variety of structural motifs concurrently within the S1-pocket. That was no surprise as the glutamate portion of L1 was expected to orient in the S1'-pocket in a fashion similar to that of the known PSMA inhibitors (e.g., GPI-18431 and 2-PMPA). In particular, the α-carboxylate of glutamate, which interacts with Arg 210, is known to be essential for PSMA binding (Mlcochova, P.; et al. *Febs J* 2007, 274, 4731-4741). L1 was superimposed with GPI-18431 using four tether attachment points in glutamate. Coordinates of the superimposed L1 were transferred and merged in the apo-form of 2C6C, in which the ligand GPI-18431 was removed.

Molecular dynamics simulation of the merged PSMA/L1 complex was performed with Generalized Born with a simple Switching (GBSW) as an implicit solvent model. Amino acid residues within 7 Å of L1 remained flexible while all other amino acids were constrained. The location of the carboxylic acid in the lysine portion of L1 dramatically changed and strongly interacted with two arginines (Arg 534 and Arg 536, FIG. 1A) after molecular dynamics simulation, while the two carboxylic acids of glutamate changed only slightly. The linear-type linker of initial L1 was grooved for maximizing interaction with the tunnel region of PSMA, i.e., the flexible linear-type linker of initial L1 adopted a compact conformation, thus enhancing the interaction of L1 with the tunnel region of PSMA after molecular dynamics simulations (FIG. 1B). From this PSMA/L1 model, the α-carboxylate of glutamate demonstrated hydrogen bonding interactions with Arg 210, Tyr 552 and Tyr 700 and the γ-carboxylate did similarly with Asn 257 and Lys 699. In addition, the two NH groups of the urea contribute to interaction with Gly 518.

Radiochemistry.

Radiolabeling with $[^{99m}Tc(CO)_3(OH_2)_3]^+$ was performed using the commercially available Isolink kit at ligand concentrations of $10^{-5}M$-$10^{-6}M$ with incubation times of 30 min at 95° C. Adducts were produced in high radiochemical yield (>70%) and purity (>98%). Formation of the $[^{99m}Tc(CO)_3L]^{+/0}$ (TcL1-TcL7) complexes resulted in a significant shift in the HPLC retention times (to longer) compared to those of the free ligands and $[^{99m}Tc(CO)_3(OH_2)_3]^+$, enabling the clear separation of the radiotracers.

Electronic Properties of ReL2.

Bisquinoline ligand L2 allows for the preparation of isostructural fluorescent $\{Re(CO)_3\}^+$ core complexes and radioactive $\{^{99m}Tc(CO)_3\}^+$ core complexes. Consequently, the fluorescent properties of ReL2 were investigated to determine whether the rhenium-based complexes possess suitable characteristics for use as biological probes (Stephenson, K. A.; et al. *J Am Chem Soc* 2004, 126, 8598-8599; James, S.; et al. *Bioconjug Chem* 2006, 17, 590-596). The electronic spectrum of ReL2 exhibited absorbance at 321 nm with an extinction coefficient of 17,200 $M^{-1}$. Excitation of ReL2 at 321 nm provides an intense fluorescence emission at 550 nm. The large Stokes shift is characteristic of this class of fluorophore (Di Bilio, A. J.; et al. *J Am Chem Soc* 2001, 123, 3181-3182). The emission peak is assigned to a $^3$MLCT [dπ(Re)→π* (ligand)] excited state on the basis of previous spectroscopic studies of Re(I) tricarbonyl complexes (Di Bilio, A. J.; et al. *J Am Chem Soc* 2001, 123, 3181-3182; Guo, X. Q.; et al. *Anal Chem* 1998, 70, 632-637; Guo, X. Q.; et al. *Anal Biochem* 1997, 254, 179-186; Lo, K. K.; *Commun (Camb)* 2003, 2704-2705). The fluorescence lifetime for ReL2 is 11.8 μs ($\lambda_{em}$=550 nm) in ethylene glycol under an argon atmosphere, which is sufficiently long to overcome the effects of endogenous fluorescence. Cellular autofluorescence can complicate in vitro imaging studies, however, since it occurs on the nanosecond time scale, it can be eliminated using time-gating techniques so long as the probe under investigation has a sufficiently long lifetime. The fluorescence quantum yield of ReL2 of 0.018 in ethylene glycol under argon is low but comparable to those reported for other transition-metal band fluorescence probes (Lo, K. K.; *Commun (Camb)* 2003, 2704-2705; Dattelbaum, et al. Bioconjug Chem 2000, 11, 533-536).

In Vitro Binding Studies.

The relative binding affinities of L1-L7 and ReL1-ReL7, were determined using the N-acetylated-α-linked acidic dipeptidase (NAALADase) assay as previously described. The data are presented in Table 1 (see Examples). As all compounds possess the lys-NHCONH-glu motif, structural variation derives from (a) the length of the linker between the chelator and the amide carbonyl carbon attached to the lysine moiety, (b) the chelator, which may be either the bispyridyl, bisquinoline or mixed (monopyridyl monocarboxyl) functional groups, (c) the presence or absence of a second amide function between the chelator and the first amide—attached to the lysine moiety and (d) the presence or absence of a carboxyl group either adjacent to the chelator, or adjacent to the second (linker) amide group. Immediately evident is the need for a methylene chain length longer than that provided by lysine itself, as the Re-chelated version of L6 displays the lowest PSMA inhibitory activity of all compounds measured and was not capable of imaging PMSA+ tumors. Compound L5 demonstrates that linkers containing seven methylene units between the chelator nitrogen and the amide carbonyl provide compounds of low nanomolar $K_i$. Longer linkers can also be accommodated easily (L4 and L7). Introduction of rhenium does not cause a consistent change in inhibitory activity, with Re-labeled versions only of L1, L4 and L5 demonstrating higher inhibitory activities than the corresponding unchelated compounds. Introduction of the $Re(CO)_3$ core/moiety to chelators of this class forces the chelator into a facial configuration, with unpredictable effects on binding to the active site. Placing the carboxylate adjacent to the chelator (L3), rather than adjacent to the amide nitrogen on the linker (L1) caused an increase in inhibitory activity of over an order of magnitude for the unchelated versions, although the Re-labeled versions were comparable. The bisquinoline chelator, which is much less polar than the bispyridyl, provides correspondingly stronger PSMA inhibitory activity. Replacing one of the pyridines with a carboxylic acid moiety (L7 to L4) causes a six-fold increase in inhibitory activity for the unchelated molecules, but a 12-fold decrease in activity for the more biologically relevant Re-labeled compounds.

Ex Vivo Biodistribution.

Compounds $[^{99m}Tc]L1$-L3 were assessed for their pharmacokinetics ex vivo in severe-combined immunodeficient (SCID) mice bearing both PSMA+ PC3 PIP and PSMA− flu xenografts (Chang, S. S.; et al. *Cancer Res* 1999, 59, 3192-3198; Foss, C. A.; et al. *Clin Cancer Res* 2005, 11, 4022-4028). Tables 2-4 (see Examples) show the percent injected dose per gram (% ID/g) uptake values in selected organs for compounds $[^{99m}Tc]L1$-L3, respectively. Compound $[^{99m}Tc]L1$ showed clear PSMA-dependant binding in PC3 PIP tumor xenografts, reaching a maximum uptake, among times investigated, of 7.87±3.95% ID/g at 30 min postinjection (p.i.). PSMA+ tumor to PSMA− tumor (PIP:flu) uptake ratios ranged from 23 at 30 min p.i. to a high of 68 at 300 min p.i. The distribution within normal organs and tissues was also favorable with low nonspecific tissue uptake and rapid clearance. The highest nonspecific uptake observed was in the spleen at 30 min p.i. and was 10.59±6.05% ID/g, which decreased to 1.81±1.10 by 60 min p.i. Kidney uptake, chiefly due to high expression of PSMA within proximal tubules, was expectedly high and peaked at 95.66±22.06% ID/g at 30 min and cleared to 1.26±0.67% ID/g by 300 min p.i.

Compound $[^{99m}Tc]L2$ was also assayed for its pharmacokinetic characteristics in tumor-bearing mice, although only at 30 and 60 min p.i. Table 3 shows the % ID/g of uptake for this radioligand. As for $[^{99m}Tc]L1$, $[^{99m}Tc]L2$ showed PSMA-dependant tumor uptake, which peaked at 60 min p.i. at 2.04±0.25% ID/g. That is significantly lower than the uptake observed for $[^{99m}Tc]L1$ in the PC3 PIP tumor. The PIP:muscle ratios were also significantly lower, achieving a maximum value of only 7.7 at 60 min p.i. as opposed to a maximum of 41.4 for $[^{99m}Tc]L1$ at 120 min p.i. It is believed that the added lipophilicity of the bisquinoline moiety contributes to additional nonspecific binding (note relatively high liver uptake at 60 min p.i. (1.15±0.33% ID/g for $[^{99m}Tc]L2$ vs 0.25±0.15% ID/g for $[^{99m}Tc]L1$) as well as the very high spleen uptake at that same time point (15.32±6.64% ID/g)). Spleen had not yet reached equilibrium during the 60 min time course of this study. Kidney uptake at 60 min p.i. was 86.0±13.9% ID/g, similar in value to that seen for $[^{99m}Tc]L1$.

Compound [$^{99m}$Tc]L3 also demonstrated PSMA-dependant tumor uptake, displaying highest PSMA+ PIP uptake at 30 min p.i. (11.56±2.86% ID/g) (Table 4). PIP:flu ratios were highest at 30 min p.i. at 21.99 and then held steady at around 5:1 through 300 min p.i. In this regard, both [$^{99m}$Tc]L2 and [$^{99m}$Tc]L3 are inferior in providing high PIP:flu ratios—the key criterion for PSMA-mediated imaging—as compared with [$^{99m}$Tc]L1. Compound [$^{99m}$Tc]L3 exhibited a similar trend in liver, lung and spleen as [$^{99m}$Tc]L1 and [$^{99m}$Tc]L2. Radiotracer uptake within spleen and liver (nonspecific binding) were also very high for [$^{99m}$Tc]L3. PSMA-mediated kidney uptake was also similar to the other compounds of this class, and peaked at 178.56±35.45 at 60 min p.i.

Metabolism.

Except for mouse kidney extracted 60 min after injection of [$^{99m}$Tc]L1, which contained 2% of its extracted radioactivity as a polar metabolite, all of the other tissue extracts, plasma and urine at 30 and 60 min postinjection contained 100% of the chromatographed radioactivity as the parent compound.

Microscopy.

Figure 2:
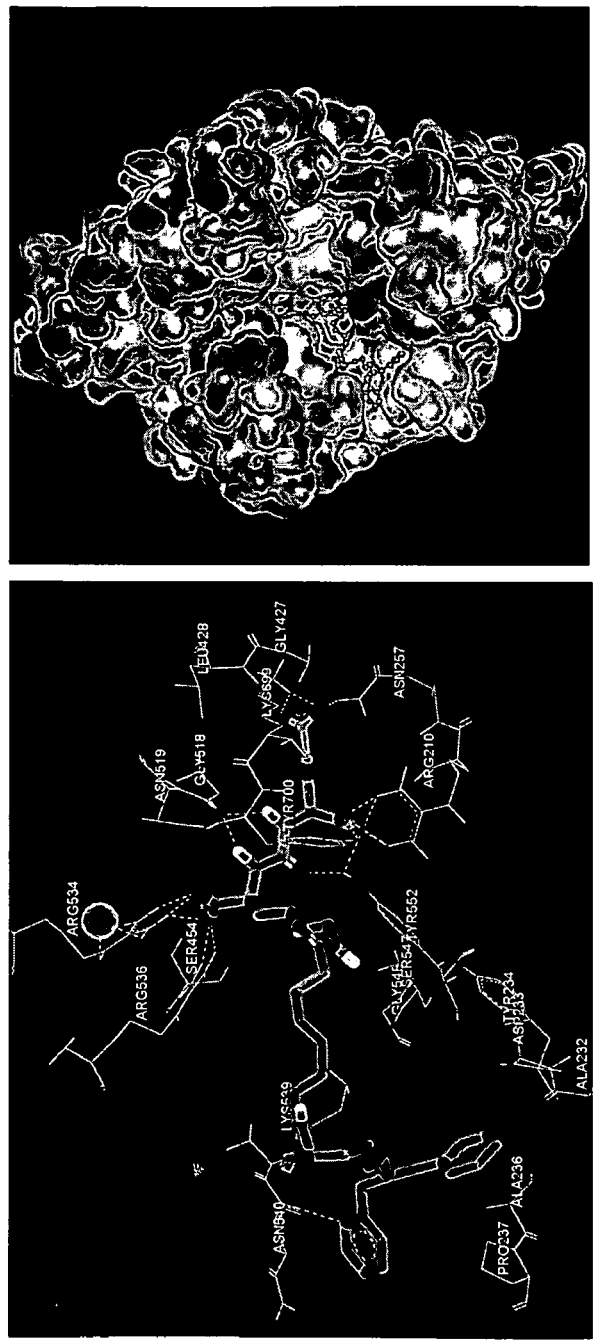
FIG. 2. Binding mode of L1 to the active site of PSMA (A). The corresponding contour map is shown in B.

Coordination of the bisquinoline moiety of L2 with Re(CO)$_3$ renders this complex fluorescent. Accordingly, microscopy was performed using ReL2 in live cells (FIG. 2). Because the Stokes shift for ReL2 is relatively large, it was necessary to excite at 494 nm and collect emission fluorescence at 628 nm. Efforts to excite at 321 nm, where the quantum efficiency for this ligand was expected to be highest, resulted in extreme autofluorescence and no useable data. Excitation in the green region of the spectrum, however, led to a weak but observable fluorescent signal from within the PSMA+ PC3 PIP cells. This result provides visual confirmation of internalization of low molecular weight ligands for PSMA. The mechanism of internalization of PSMA has been studied previously, however only antibodies and antibody conjugates have been used, rather than small molecules (Rajasekaran, S. A.; et al. *Mol Biol Cell* 2003, 14, 4835-4845; Moffatt, S.; et al. *Gene Ther* 2006, 13, 761-772).

Imaging.

Figure 3:
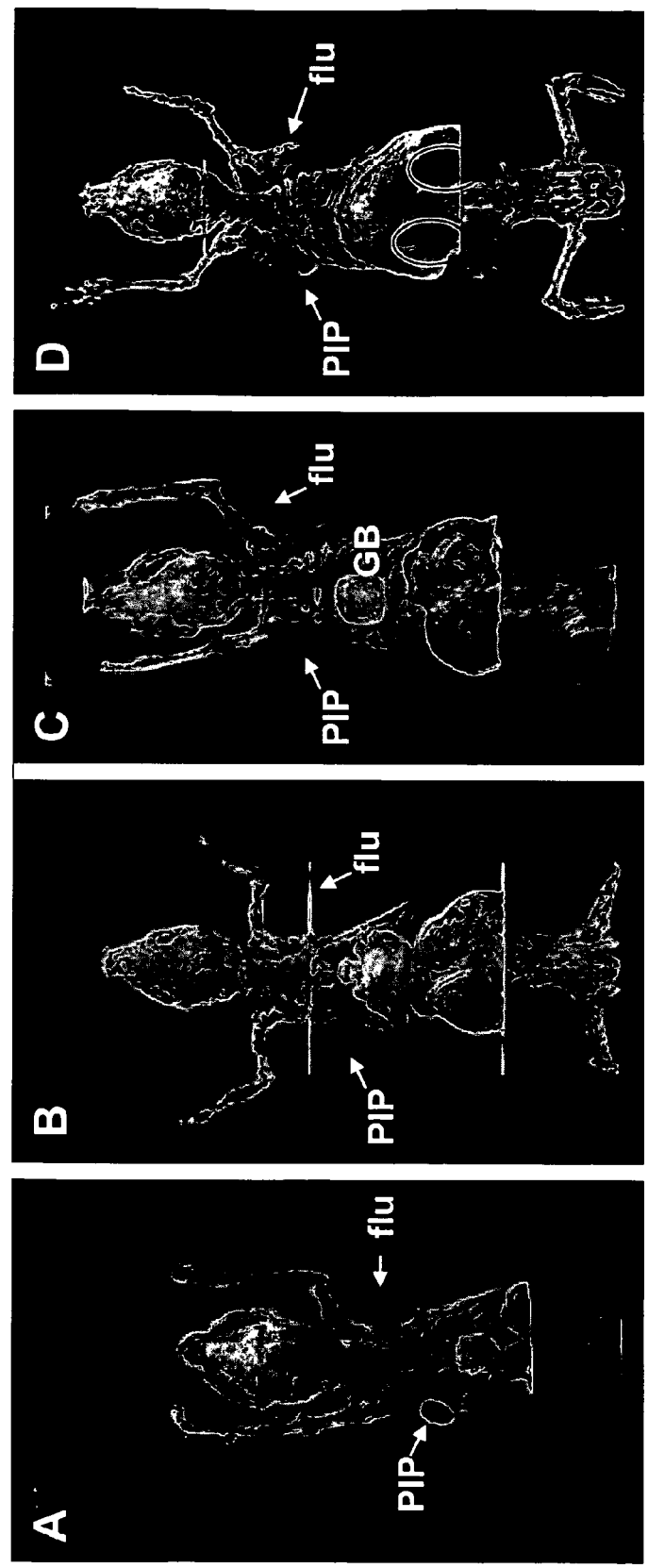
FIG. 3. SPECT-CT imaging of tumor bearing mice with [$^{99m}$Tc]L1-L4 (A-D, respectively). Dual pinhole SPECT-CT of PC-3 PIP and PC-3 flu tumor bearing mice. Mice were injected with 0.5-1 mCi (19-37 MBq) of radiopharmaceutical i.v. followed by a 45 min uptake period. Note essentially no uptake in the PSMA− flu tumors in each case. Abdominal radioactivity is primarily due to uptake within liver, spleen and kidneys. The horizontal lines in B are due to a reconstruction artifact at the boundaries of the field-of-view. PIP=PC-3 PIP; flu=PC-3 flu; GB=gallbladder in C; red circles highlight the location of the kidneys in D; L=left, R=right.
Figure 4:
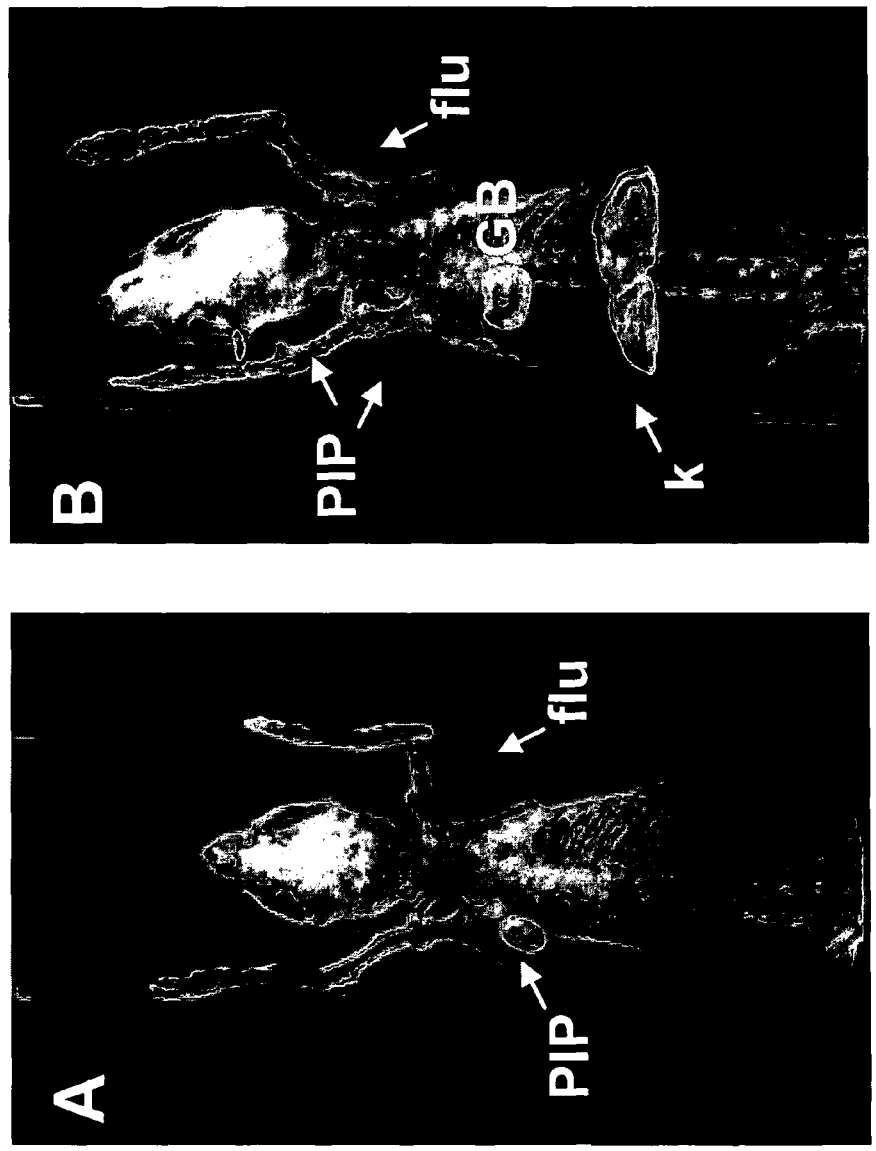
FIG. 4. SPECT-CT imaging of tumor bearing mice with [$^{99m}$Tc]L1 and [$^{99m}$Tc]L3 (A and B, respectively). Dual pinhole SPECT-CT of PC-3 PIP and PC-3 flu tumor bearing mice. Mice were injected with 0.5-1 mCi (19-37 MBq) of radiopharmaceutical i.v. followed by a 3.5-4 h uptake period. Note lack of radiopharmaceutical outside of tumor in A; however, the kidneys are outside of the field of view.

SPECT-CT imaging was carried out in SCID mice. Each mouse had a PSMA+ PC3 PIP and PSMA− PC3 flu xenograft in opposite, upper flanks. All radioligands were screened this way and the results obtained were used to determine whether ex vivo biodistribution assay would add further information. FIG. 3 shows early, rendered images of mice with radioligands that demonstrated positive PIP tumor uptake. Mice were injected intravenously with 0.5-1 mCi (19-37 MBq) of the corresponding $^{99m}$Tc-labeled compound and were imaged at 45 min p.i. Successful radioligands enabled visualization of both the PIP tumor and the kidneys, each of which expresses PSMA. Compounds [$^{99m}$Tc]L1-L4 yielded positive scans with distinguishing features. Compound [$^{99m}$Tc]L1 showed a strongly positive PIP tumor, gallbladder uptake and clear visualization of the kidneys. Compound [$^{99m}$Tc]L2 showed weak PIP tumor uptake, strong gallbladder uptake and kidney uptake. Compound [$^{99m}$Tc]L3 showed strong PIP tumor uptake, despite the small size of the tumor, gallbladder uptake and clear visualization of the kidneys. Compound [$^{99m}$Tc]L4 showed elevated PIP tumor uptake as well as high liver and kidney uptake. Images obtained several hours after injection of [$^{99m}$Tc]L1 or [$^{99m}$Tc]L3 demonstrated higher contrast of tumor with respect to background (FIG. 4), with very little radioactivity evident outside of the tumor for [$^{99m}$Tc]L1. Compound [$^{99m}$Tc]L5 produced images qualitatively similar to [$^{99m}$Tc]L4.

Figure 5:
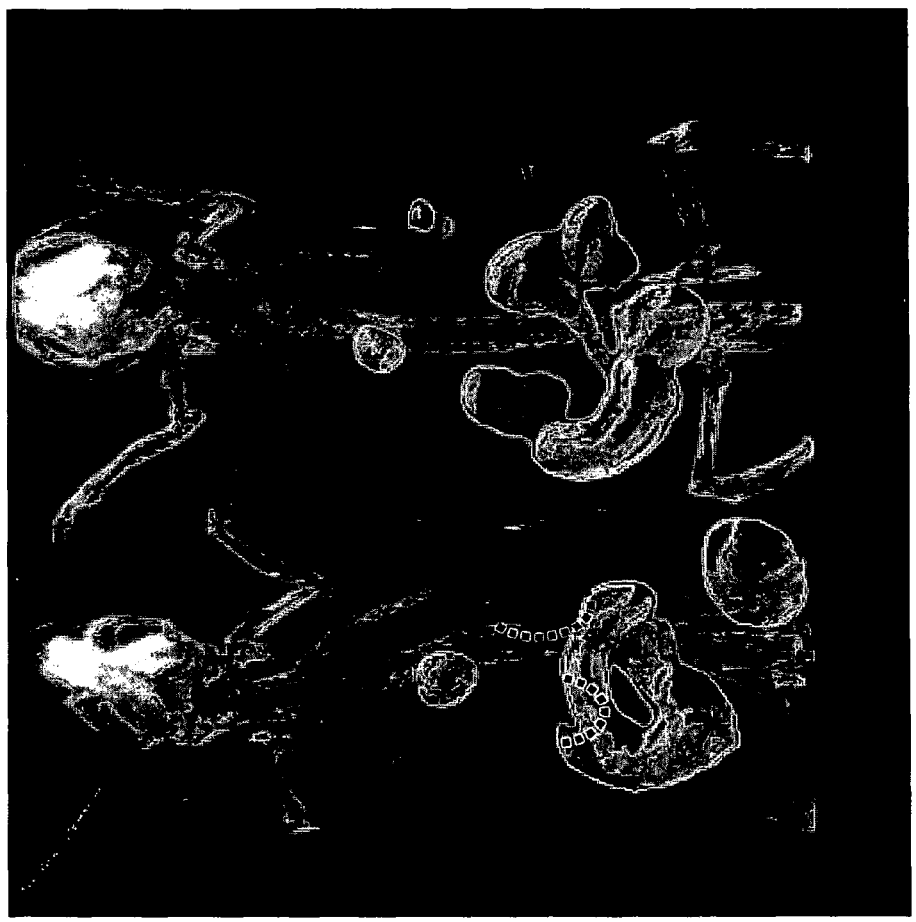
FIG. 5. SPECT-CT imaging of LNCaP (PSMA+) tumor bearing mice with [$^{99m}$Tc]L1 with (left) and without (right) blockade of PSMA using the potent, selective PSMA inhibitor, PMPA, as the blocking agent. Lack of radiopharmaceutical in both the tumor and kidneys (another PSMA+ site) upon co-treatment with PMPA provides a further check on PSMA-specific binding. Images were acquired from 30-60 min postinjection. T=tumor; K=kidney.
Figure 6:
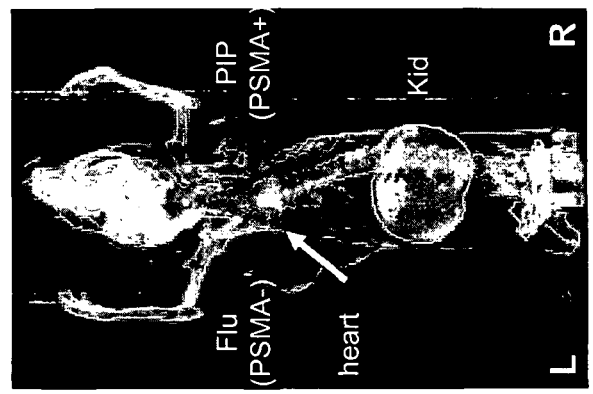
FIG. 6. SPECT-CT imaging of tumor bearing mouse with [$^{111}$In]-DOTA-L1. Dual pinhole SPECT-CT of PC-3 PIP and PC-3 flu tumor bearing mouse. Mouse was injected with 0.5 mCi (19 MBq) of radiopharmaceutical i.v. followed by a 3.5-4 h uptake period.

As a further test of in vivo binding specificity, we performed a blocking study using [$^{99m}$Tc]L1 in an LNCaP (PSMA+) prostate tumor model, but first pretreating the animal with 50 mg/kg of the potent, selective PSMA inhibitor, 2-(phosphonomethyl)pentanedioic acid (PMPA). FIG. 5 shows that PMPA is capable of eliminating binding of [$^{99m}$Tc]L1 not only to tumor, but also to renal cortex, another site of specific binding for radiopharmaceuticals of this class. These results provide one more check on in vivo binding selectivity, using a blocking agent from a different chemical class than the urea-based inhibitors, and in a different, well-established, PSMA+ prostate tumor.

Despite advances using a variety of imaging modalities, most notably MR spectroscopy, clinically viable molecular imaging of PCa has remained elusive. FDG-PET, which has worked so well not only for identification of primary and metastatic tumors, but also for therapeutic monitoring, has largely failed in the case of PCa, perhaps due to the relatively low rate of metabolism of these tumors compared to other epithelial cancers. Although iterative reconstruction with anatomic coregistration can improve ProstaScint™ imaging, and using a radiolabeled version of the J591 human monoclonal antibody against an extracellular epitope of PSMA show some promise, these agents will be fraught with the same disadvantages of all intact antibodies for imaging, namely slow clearance from blood and nonspecific sites. Nevertheless, these antibodies bind to what we consider an ideal target for prostate cancer imaging and therapy—PSMA.

The radiopharmaceuticals described by the invention here are part of a series of new low molecular weight PSMA-based imaging agents. It has been previously demonstrated the specific binding of suitably functionalized ureas to PSMA, for imaging with SPECT and PET. However those agents were radiolabeled with either $^{125}$I, $^{11}$C or $^{18}$F (Foss, C. A.; et al. *Clin Cancer Res* 2005, 11, 4022-4028; Pomper, M. G.; et al. *Mol Imaging* 2002, 1, 96-101; Mease R. C. et al. Clin Cancer Res. 2008, 14, 3036-3043). Iodine-125-labeled agents can be used in conjunction with high-resolution small animal imaging devices to study experimental models and the isotope can be switched to $^{123}$I or $^{124}$I for human SPECT or PET, respectively. However, those isotopes are expensive ($1,000/mCi for [$^{124}$I]NaI) and can be difficult to obtain on short notice. Carbon-11 is largely an experimental radionuclide for use only at centers that have a cyclotron in-house. Fluorine-18-labeled radiopharmaceuticals can be shipped limited distances, but those compounds will be of relatively low specific radioactivity upon arrival at the site of usage. Fluorine-18 also requires a cyclotron for production. For these reasons, the ready availability (via generators delivered to nuclear medicine departments daily) and ideal imaging characteristics of $^{99m}$Tc, we have embarked on a program to synthesize $^{99m}$Tc-labeled PSMA-based imaging agents. It was found that using SAAC technology, $^{99m}$Tc can be readily incorporated in a sterically unobtrusive manner to these PSMA-binding ureas. Because Tc has no stable isotope, we used the group VIIB congener Re for the PSMA inhibitory studies.

Various compounds were synthesized, designated L1-L7, in both their Re— and $^{99m}$Tc-labeled forms. These seven compounds derive from DCL, with different linkers between the ε amine of lysine and the chelator. Using SAAC technology, three different chelators were generated, namely the bispyridyl, the bisquinoline and monopyridyl-monoacid. The primary rationale for the use of these different chelators was to exploit their differing degrees of steric bulk and lipophilicity. Both L1 and L2 provide cationic complexes upon complexation with the organometallic $^{99m}$Tc(CO)$_3$/Re(CO)$_3$ core. On the other hand, L4 offers a neutral complex for the metal tricarbonyl core. Compound L2 provides the most lipophilic agent (Table 1). That degree of lipophilicity had a significant effect on both the in vitro binding as well as the in vivo imaging, with ReL2 demonstrating 20-fold higher PSMA inhibitory activity than ReL1, but six-fold lower PIP:flu at 1 h postinjection and significantly more liver and spleen uptake for the $^{99m}$Tc analog (Table 1, FIG. 3). PIP and flu tumors are derived from PC3 human prostate cancer cells that differ only in their expression of PSMA (PIP=PSMA+, flu=PSMA−). Another way to alter the lipophilicity of these complexes is to introduce a carboxylic acid moiety to various positions on the linker. Moving the linker carboxylic acid to the carbon adjacent to the chelator nitrogen caused the binding affinity to drop (ReL3), and provide lower PIP:flu and higher liver and spleen uptake than compound [$^{99m}$Tc]L1 (FIG. 3). In this series of three compounds, [$^{99m}$Tc]L1 has the best properties for imaging in vivo, despite its relatively low PSMA inhibitory potency.

Compounds ReL4 and ReL7 enable comparison of the bispyridyl and monopyridyl-monoacid chelators, respectively. Compound ReL4 had a PSMA inhibitory potency of about 12-fold higher than that of ReL7. Although ex vivo biodistribution assays were not performed for these two compounds, [$^{99m}$Tc]L4 demonstrated strong uptake in PIP as opposed to flu tumors, but there was also significant uptake within liver—an undesirable imaging characteristic perhaps due to the increased lipophilicity of this compound relative to [$^{99m}$Tc]L1 and [$^{99m}$Tc]L3, which have a slightly shorter linker length and incorporates a linker acid moiety (FIG. 3). Compound [$^{99m}$Tc]L7 demonstrated no evidence of specific PIP tumor uptake and showed only radioactivity within the liver.

Compound L5 has no amide or carboxylic acid within the linker and L6 has the bispyridyl incorporated into the ε amine of lysine. The linker chain of L5 is six carbons shorter than that of the L1-L3 series. Compound ReL6 demonstrated very low PSMA inhibitory activity, the lowest in the entire series, and [$^{99m}$Tc]L6 showed no PIP tumor-specific uptake.

In this series [$^{99m}$Tc]L1 and ReL2 have emerged as providing utility for imaging prostate cancer in vivo and in vitro, respectively. Compound [$^{99m}$Tc]L1 is a promising clinical candidate because of its synthetic accessibility, very high target to nontarget ratio (PIP:flu=44:1 at 2 h postinjection), rapid washout kinetics, metabolic stability and the many salutary characteristics of $^{99m}$Tc discussed above. The initial indication for its use would be to study patients who have undergone prostatectomy in whom a rising prostate-specific antigen (PSA) is detected—the same indication as for ProstaScint™. Compound ReL2 has documented the internalization of PSMA after binding of a low molecular weight agent to the active site (FIG. 2). This compound could be used to study the kinetics of PSMA internalization. The internalization of compounds of this class suggests the development of the corresponding radiotherapeutic analogs.

Chemical Description and Terminology

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and R* at each occurrence is selected independently from the definition of R*. Also, combinations of substituents and/or variables are permissible only if such combinations result in stable compounds.

As indicated above, various substituents of the various formulae are "optionally substituted". The term "substituted," as used herein, means that any one or more hydrogens on the designated atom or group is replaced with a selection from the indicated group of substituents, provided that the designated atom's normal valence is not exceeded, and that the substitution results in a stable compound. When a substituent is oxo (keto, i.e., =O), then 2 hydrogens on an atom are replaced. The present invention is intended to include all isotopes (including radioisotopes) of atoms occurring in the present compounds.

When are further substituted, they may be so substituted at one or more available positions, typically 1 to 3 or 4 positions, by one or more suitable groups such as those disclosed herein. Suitable groups that may be present on a "substituted" group include e.g., halogen; cyano; hydroxyl; nitro; azido; alkanoyl (such as a $C_{1-6}$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; carbocyclic aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_{1-6}$ alkyl groups. Especially preferred alkyl groups are methyl, ethyl, propyl, butyl, and 3-pentyl. The term $C_{1-4}$ alkyl as used herein includes alkyl groups consisting of 1 to 4 carbon atoms, which may contain a cyclopropyl moiety. Suitable examples are methyl, ethyl, and cyclopropylmethyl.

"Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "$(C_{3-8}$ cycloalkyl$)C_{1-4}$ alkyl", cycloalkyl, and alkyl are as defined above, and the point of attachment is on the alkyl group. This term encompasses, but is not limited to, cyclopropylmethyl, cyclohexylmethyl, and cyclohexylmethyl.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 8 carbon atoms, more typically 1 to about 6 carbon atoms.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Alkoxy groups typically have 1 to about 8 carbon atoms, more typically 1 to about 6 carbon atoms.

"Halolkoxy" represents a haloalkyl group as defined above with the indicated number of carbon atoms attached through an oxygen bridge.

As used herein, the term "alkylthio" includes those groups having one or more thioether linkages and preferably from 1 to about 8 carbon atoms, more typically 1 to about 6 carbon atoms.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylamino" includes those groups having one or more primary, secondary and/or tertiary amine groups and typically from 1 to about 8 carbon atoms, more typically 1 to about 6 carbon atoms.

"Halo" or "halogen" as used herein refers to fluoro, chloro, bromo, or iodo; and "counter-ion" is used to represent a small, negatively charged species such as chloride, bromide, hydroxide, acetate, sulfate, and the like.

As used herein, "carbocyclic group" is intended to mean any stable 3- to 7-membered monocyclic or bicyclic or 7- to 13-membered bicyclic or tricyclic group, any of which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, phenyl, naphthyl, indanyl, and tetrahydronaphthyl.

As used herein, the term "heterocyclic group" is intended to include saturated, partially unsaturated, or unsaturated (aromatic) groups having 1 to 3 (preferably fused) rings with 3 to about 8 members per ring at least one ring containing an atom selected from N, O or S. The nitrogen and sulfur heteroatoms may optionally be oxidized. The term or "heterocycloalkyl" is used to refer to saturated heterocyclic groups.

The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. As used herein, the term "aromatic heterocyclic system" is intended to include any stable 5- to 7-membered monocyclic or 10- to 14-membered bicyclic heterocyclic aromatic ring system which comprises carbon atoms and from 1 to 4 heteroatoms independently selected from the group consisting of N, O and S. It is preferred that the total number of S and O atoms in the aromatic heterocycle is not more than 2, more preferably not more than 1.

Examples of heterocycles include, but are not limited to, those exemplified elsewhere herein and further include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl. Also included are fused ring and spiro compounds containing, for example, the above heterocycles.

As used herein, the term "carbocyclic aryl" includes groups that contain 1 to 3 separate or fused rings and from 6 to about 18 ring atoms, without hetero atoms as ring members. Specifically preferred carbocyclic aryl groups include phenyl, and naphthyl including 1-napthyl and 2-naphthyl.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)$n-COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

The contents of all cited references (including literature references, issued patents, published patent applications) as cited throughout this application are hereby expressly incorporated by reference.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

EXAMPLES

The present invention is further illustrated by the following examples which should not be construed as limiting in any way. The practice of the present invention will employ, unless otherwise indicated, conventional techniques, which are within the skill of the art. Such techniques are explained fully in the literature.

General Procedures. All reactions were performed under a nitrogen atmosphere unless otherwise noted. Solvents and chemicals obtained from commercial sources were of analytical grade or better and used without further purification. All experiments were performed in duplicate or triplicate to ensure reproducibility. Analytical thin-layer chromatography (TLC) was performed using Aldrich aluminum-backed 0.2 mm silica gel Z19, 329-1 plates and visualized by ultraviolet light (254 nm), $I_2$ and 1% ninhydrin in EtOH. Flash chromatography was performed using silica gel purchased from Bodman (Aston Pa.), MP SiliTech 32-63 D 60 Å. In most cases product isolation consisted of removing of the solvent from the reaction mixture, extracting with an organic solvent, washing with water and brine, drying with anhydrous sodium sulfate, filtering, and concentrating the filtrate. The use of such workup conditions will be indicated by the phrase "product isolation" (which is followed, in parentheses, by the extracting solvent). Purification in most cases was achieved by flash chromatography and is signified by the term "flash chromatography" (which is followed, in parentheses, by the elution solvent used). Melting points were measured using a Mel-Temp apparatus and are uncorrected. $^1$H NMR spectra were recorded on either a Varian Mercury 400 MHz or on a Bruker Ultrashield™ 400 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. Higher-resolution FAB mass spectra were obtained on a JOEL JMS-AX505HA mass spectrometer in the mass spectrometer facility at the University of Notre Dame. Optical rotation was measured on a Jasco P-1010 polarimeter. Infrared spectra were obtained on a Bruker Tensor 27 spectrometer. High-performance liquid chromatography (HPLC) purification of L1-L7 and ReL1-ReL7 using a Phenomenex $C_{18}$ Luna 10×250 mm$^2$ column was performed on a Waters 600E Delta LC system with a Waters 486 tunable absorbance UV/Vis detector, both controlled by Empower software. Purification of ReL1-L7 and [$^{99m}$Tc]L1-L7 by HPLC was performed using the following isocratic conditions: Method 1, the mobile phase was 65% solvent A (0.1% TFA in water) and 35% solvent B (0.1% TFA in $CH_3CN$), flow rate 2 mL/min; Method 2, mobile phase was 65% solvent A and 35% solvent B, flow rate 4 mL/min; Method 3, mobile phase was 70% solvent A and 30% solvent B, flow rate 2 mL/min. Eluant was monitored at 254 nm and 220 nm. For radiosynthetic purification, HPLC was performed with a Waters Chromatography Division HPLC System equipped with two model 510EF pumps, a model 680 automated gradient controller, a model 490 UV absorbance detector, and a Bioscan NaI scintillation detector connected to a Bioscan Flow-count system. The output from the UV detector and the Flow-count radiodetector system were fed into a Gateway 2000 P5-133 computer fitted with an IN/US System, Inc. computer card and analyzed using Winflow software (IN/US). Absorption spectra were collected using a Hewlett-Packard 8453 spectrophotometer. The Isolink kit was a generous gift from Mallinckrodt-Tyco Health Care (St. Louis, Mo., USA).

Example 1

Synthesis of Intermediates

2-Amino-6-tert-butoxycarbonylamino-hexanoic acid 4-methoxy-benzyl ester (2)

Compound 2 was prepared in two steps. Into a 250 mL, flame dried three necked round bottom flask under nitrogen was placed $N_\epsilon$-Boc-$N_\alpha$-Fmoc-L-lysine (7.0 g, 15 mmol) and 60 mL of dry DMF. To this was added cesium carbonate (7 g, 21 mmol) and 4-methoxybenzyl chloride (2.5 g, 16 mmol). The suspension was stirred at room temperature under nitrogen for 4 h, then filtered and washed with ethyl acetate. Product isolation (EtOAc, 5% $Na_2CO_3$, water, $Na_2SO_4$) followed by recrystallization from 60/40 (v/v) hexane/EtOAc gave 2 crops of a colorless solid. mp 118-120° C. TLC $R_f$=0.33 (70/30 Hexane/EtOAc). Yield: 8.22 g, 14 mmol, 93.43%. $^1$H NMR($CDCl_3$) δ: 7.75 (d, J=7.2 Hz, 2H), 7.55 (d, J=7.2 Hz, 2H), 7.38 (t, J=7.5 Hz, 2H), 7.32-7.20 (m, 4H), 6.85-6.80 (m, 2H), 5.4 (d, J=7.6 Hz, 1H), 5.18-5.00 (m, 2H), 4.44-4.38 (m, 3H), 4.17 (t, J=6.0 Hz 1H), 3.80-3.70 (m, 4H), 3.00 (m, 2H), 1.90-1.11 (m, 15H). ESIMS m/z: 588.40 $[M+1]^+$.

Into a flame dried round bottom flask was placed 5.0 g (8.54 mmol) of the fully protected analog of 2. This was dissolved in 60 mL of a 20% solution of piperidine in DMF. The reaction was stirred at room temperature for 2 h. Product isolation ($CH_2Cl_2$, water, $Na_2SO_4$) followed by flash chromatography (4/96 MeOH/$CHCl_3$) afforded a pure 2 as an oil (2.59 g, 7.07 mmol) in 83% yield. (TLC $R_f$=0.42 in 5/95 MeOH/$CH_2Cl_2$). $^1$H NMR ($CDCl_3$) δ: 7.29 (d, J=7.2 Hz, 2H), 6.90 (d, J=7.2 Hz, 2H), 5.09 (m, 2H), 4.44-4.24 (m, 1H), 3.83 (s, 3H), 2.76-58 (m, 3H), 2.11-1.34 (m, 16H). ESIMS m/z: 367$[M+1]^+$ for $C_{19}H_{31}N_2O_5$.

2-{3-[1-p-methoxybenzylcarboxylate-(5-t-butylcarbamylpentyl)]-ureido}-di-p-methoxybenzyl pentanedioate (3)

Bis-4-methoxybenzyl-L-glutamate HCl 4 (3.6 g, 8.5 mmol) was placed in a flame dried 3-neck round bottom flask under nitrogen and dissolved in 15 mL $CH_2Cl_2$. Triphosgene (0.833 g, 2.8 mmol) was placed in a vial, dissolved in 3 mL $CH_2Cl_2$ and added to the three neck flask. The flask was cooled to −77° C. (dry ice ethanol slurry) under nitrogen. To this was slowly added triethylamine (12 ml, 85 mmol in 10 ml $CH_2Cl_2$). The reaction mixture was stirred at −77° C. for 1 h, allowed to warm to room temperature and was stirred for 30 min at rt. To this was added compound 2 (3.1 g, 8.5 mmol in 7 mL $CH_2Cl_2$). The resulting mixture was stirred overnight. Product isolation ($CH_2Cl_2$, water, NaCl, $Na_2SO_4$) followed by flash chromatography (20/80 EtOAc/$CH_2Cl_2$) afforded an oil that solidified upon standing. Yield: 4.135 g, 5.3 mmol, 62.3%. TLC $R_f$=0.47 (20/80 EtOAc/$CH_2Cl_2$). $^1$H NMR ($CDCl_3$) δ: 7.26-7.2 (m, 6H), 6.86-6.80 (m, 6H), 5.89 (m, 2H), 5.12-5.0 (m, 6H), 4.51 (m, 1H), 4.45 (m, 1H), 3.77 (s, 9H), 2.98 (m, 2H), 2.36 (m, 2H), 2.12 (m, 1H), 1.92 (m, 1H), 1.70 (m, 1H), 1.58 (m, 1H), 1.4 (m, 11H), 1.24 (m, 3H); ESIMS m/z: 780 $[M+1]^+$, HRFAB$^+$-MS: Calcd for $C_{41}H_{54}N_3O_{12}$, 780.3679, $[M+1]^+$, observed 780.3685 $[M+1]^+$; $^{25}[\alpha]_D$=−3.440 (0.12, DMF).

p-Toluenesulfonate salt of 2-{3-[1-p-methoxybenzylcarboxylate-(5-aminopentyl)]-ureido}-di-p-methoxybenzyl pentanedioate, (5)

A solution of 3 (2 g, 2.6 mmol) dissolved in 20 mL EtOAc was cooled to 0-2° C. in an ice bath and p-toluenesulfonic acid monohydrate (0.49 g, 2.6 mmol) in 5 mL of absolute ethanol was added. The cooling bath was removed and the reaction mixture was allowed to warm to room temperature for 2 h. The reaction mixture was then concentrated to a thick oil under reduced pressure and the mixture was purified with flash chromatography using 10/90 MeOH/$CH_2Cl_2$ to afford product as colorless solid in 45% (0.98 g, 1.15 mmol) yield. TLC $R_f$=0.47 (10/90 MeOH/$CH_2Cl_2$). $^1$H NMR ($CDCl_3$) δ: 7.68 (d, J=8.0 Hz, 2H), 7.66-7.57 (s, broad, 3H), 7.22-7.13 (m, 6H), 7.0 (d, J=7.2 Hz, 2H), 6.84-6.76 (m, 6H), 6.34 (s broad, 2H), 5.06-4.88 (m, 6H), 4.44 (m, 1H), 4.32 (m, 1H), 3.76 (s, 3H), 3.73 (s, 6H), 2.86 (s, broad, 2H), 2.3-2.24 (singlet on top of multiplet, 5H), 2.08-1.99 (m, 1H), 1.82-1.72 (m, 1H), 1.64-1.3 (m, 6H); ESIMS m/z: 680 $[M^++1]$, HRFAB$^+$-MS: Calcd for $C_{36}H_{46}N_3O_{10}$, 680.3178 $[M^+]$, found: 680.3177.

2-{3-[1-p-Methoxybenzylcarboxylate-(5-aminopentyl)]-ureido}-di-p-methoxybenzyl pentanedioate (1)

A solution of 5 (0.15 g, 0.17 mmol in 50 mL $CH_2Cl_2$) was placed in a separatory funnel, washed with 100 mL 0.5 M $NaHCO_3$. The organic layer was collected, dried over anhydrous $Na_2SO_4$, filtered, and concentrated to a yellow film (0.107 g, 0.09 mmol, 52.5%). TLC $R_f$=0.40 (10/90 MeOH/$CH_2Cl_2$) $^1$H NMR ($CDCl_3$) δ: 7.2-7.12 (m, 6H), 6.8-6.72 (m, 6H), 5.84 (s broad, 2H), 5.04-4.90 (m, 6H), 4.44-4.34 (m, 2H), 3.7 (m, 9H), 2.6 (s broad, 2H), 2.3 (m, 2H), 2.06 (m, 1H), 1.85 (m, 1H), 1.66 (m, 1H), 1.55 (m, 1H), 1.44-1.12 (m, 4H). ESIMS: 680 $[M+1]^+$. Compound 1 was used immediately in the next step.

2-{3-[5-[7-(2,5-Dioxo-pyrrolidin-1-yloxycarbonyl)-heptanoylamino]-1-(4-methoxy-benzyloxycarbonyl)-pentyl]-ureido}-pentanedioic acid bis-(4-methoxy-benzyl)ester (6)

A 100 mL round bottom flask was flame dried under $N_2$, after which 1 (0.08 g, 0.12 mmol) was added and then dissolved in 10 mL of dry DMF. This solution was added dropwise to a solution of suberic acid bis-(N-hydroxysuccinimide ester), DSS, (0.13 g, 0.35 mmol in 10 mL DMF) at room temperature with mild stirring. After 2 h, the volume of the solution was reduced under vacuum and the colorless solid residue was kept under high vacuum for 2 h further to remove traces of DMF. The residue was dissolved in 1 mL of $CH_2Cl_2$ and was loaded onto silica gel column (1 inch×12 inch). Initially the column was eluted with 40/60 $CH_3CN/CH_2Cl_2$ to remove excess DSS followed by 50/50 $CH_3CN/CH_2Cl_2$ to afford the product as a colorless solid. Yield: 0.062 mg, 0.07 mmol, 56.6%. TLC $R_f$=0.47 (5/95 MeOH/$CH_2Cl_2$) $^1$H NMR ($CDCl_3$) δ: 7.26 (m, 6H), 6.86 (m, 6H), 5.91 (m, 1H), 5.37 (m, 4H), 5.03 (m, 6H), 4.43 (m, 3H), 3.79 (s, 9H), 3.31 (m, 4H), 2.82 (s, 4H), 2.58 (t, J=8.4 Hz, 2H), 2.37 (m, 2H), 2.14 (m, 4H), 1.71-1.21 (m, 9H). ESIMS m/z: 933 $[M+1]$, (HRFAB$^+$-MS): Calcd for $C_{48}H_{61}N_4O_{15}$ $[M+1]^+$, 933.4133, found 933.4142 $[M+1]^+$.

Example 2

2-[3-(5-{7-[5-(Bis-pyridin-2-ylmethyl-amino)-1-carboxy-pentylcarbamoyl]-heptanoylamino}-1-carboxy-pentyl)-ureido]-pentanedioic acid (L1)

A solution of 7 (Levadala, M. K.; et al. *Synthesis* 2004, 11, 1759-1766) (0.035 g, 0.107 mmol in 0.5 mL MeOH) was added to a stirred solution of 6 (0.100 g, 0.107 mmol in 6 mL dry DMF) at room temperature followed by the addition of 0.2 mL NEt$_3$. The reaction mixture was stirred for 10 h at room temperature. The reaction mixture was then concentrated under reduced pressure. Product isolation (CH$_2$Cl$_2$, water, Na$_2$SO$_4$) followed by flash chromatography (50/50 MeOH/CH$_2$Cl$_2$) afforded the intermediate compound as a colorless solid in 74% yield (0.090 g, 0.08 mmol). TLC R$_f$=0.45 (40/60 MeOH/CH$_2$Cl$_2$). ESIMS m/z: 1146.7 [M+1]$^+$, 1168.7 [M+Na]$^+$. The above intermediate compound (20 mg, 0.017 mmol) was dissolved in an ice-cold solution of TFA (7 mL) and anisole (0.3 mL) and was stirred for 10 min. The ice bath was removed and the solution was allowed to warm to room temperature with continued stirring for another 10 min. The solution was evaporated under reduced pressure and the light brown residue was dried under high vacuum for 2 h. The residue was washed with diethyl ether (3×5 mL) and water (10×2 mL) to produce crude L1. Yield: 9 mg, 0.011 mmol, 65%. The colorless product was dried under vacuum and purified further by HPLC using 75/25 water (0.1% TFA)/acetonitrile (0.1% TFA) as mobile phase, flow rate 2 ml/min; R$_t$=14 min. $^1$H NMR (D$_2$O) δ: 8.71 (d, J=5.6 Hz, 2H), 8.52 (t, J=8 Hz, 2H), 8.05 (d, J=8 Hz, 2H), 7.96 (t, J=6.8 Hz, 2H), 4.32-4.18 (m, 7H), 3.80-3.70 (m, 1H), 3.18 (t, J=6 Hz, 2H), 2.69 (m, 2H), 2.51 (t, J=7.6 Hz, 2H), 2.40-2.18 (m, 25H). $^{13}$C NMR (D$_2$O) δ: 177.2, 177.13, 163.10, 162.8, 159.2, 152.4, 146.1, 142.3, 126.8, 126.1, 55.8, 54.4, 46.6, 38.8, 35.6, 35.2, 30.6, 30.0, 29.9, 27.7, 27.6, 26.3, 25.2, 25.0, 24.3, 22.4, 22.3. ESIMS m/z: 786 [M+1]; HRFAB$^+$-MS: Calcd. for C$_{38}$H$_{56}$N$_7$O$_{11}$[M+1], 786.4038; found: 786.4033.

Compounds L1-L3 were prepared by following the same general synthetic procedure as shown in Scheme 2 for L1 as a representative case.

Example 3

2-[3-(5-{7-[5-(Bis-quinolin-2-ylmethyl-amino)-1-carboxy-pentylcarbamoyl]-heptanoylamino}-1-carboxy-pentyl)-ureido]-pentanedioic acid (L2)

Compound L2 was obtained by reacting compound 8 (Stephenson, K. A.; et al. *J Am Chem Soc* 2004, 126, 8598-8599) with compound 6 similarly as described above for L1. HPLC purification was done by using 70/30 water (0.1% TFA)/CH$_3$CN (0.1% TFA) as mobile phase, flow rate 4 ml/min; R$_t$=9 min. $^1$H NMR (D$_2$O/CD$_3$CN 2/1) δ: 8.81 (d, J=8.0 Hz, 2H), 8.42 (d, J=8.4 Hz, 2H), 8.33 (d, J=8.4 Hz, 2H), 8.22 (t, J=7.6 Hz, 2H), 8.05 (t, J=7.8 Hz, 2H), 7.97 (d, J=8.4 Hz, 2H), 5.11 (s, 4H), 4.66-4.64 (m, 1H), 4.57-4.54 (m, 1H), 4.47-4.46 (m, 1H), 3.71 (m, 2H), 3.51-3.43 (m, 3H), 2.77 (t, J=7.6 Hz, 2H), 2.51 (m, 3H) 2.20-1.5 (m, 26H). ESIMS m/z: 902 [M+H$_2$O]; HRFAB$^+$-MS: C$_{46}$H$_{60}$N$_7$O$_{12}$ [M+H$_2$O], 902.4300; found 902.4290.

Example 4

2-[3-(5-{7-[5-(Bis-pyridin-2-ylmethyl-amino)-5-carboxy-pentylcarbamoyl]-heptanoylamino}-1-carboxy-pentyl)-ureido]-pentanedioic acid (L3)

Compound L3 was prepared by reacting compound 9 (Levadala, et al. *Synthesis* 2004, 11, 1759-1766) with compound 6 similarly as described above for L1. HPLC purification was done by using 75/25 water (0.1% TFA)/CH$_3$CN (0.1% TFA) as mobile phase, flow rate 2 mL/min, R$_t$=8 min. $^1$H NMR (D$_2$O) δ: 8.68 (d, J=6.0 Hz, 2H), 8.50 (t, J=7.6 Hz, 2H), 8.06 (d, J=5.6 Hz, J=7.9 Hz, 2H), 7.94 (t, J=6.4 Hz, 2H), 4.32-4.37 (m, 4H), 4.25 (m, 1H), 4.18 (m, 1H), 3.48 (t, J=7.2 Hz, 1H), 3.16 (m, 2H), 2.69 (m, 2H), 2.48 (t, J=7.2 Hz, 2H), 2.18-2.15 (m, 5H), 1.97-1.20 (m, 21H). ESIMS m/z: 786 [M+1]$^+$; HRFAB$^+$-MS: Calcd. for C$_{38}$H$_{55}$N$_7$O$_{11}$, 786.4038 [M+1], found: 786.4032.

Example 5

2-[3-(1-Carboxy-5-{7-[6-(carboxymethyl-pyridin-2-ylmethyl-amino)-hexylcarbamoyl]-heptanoylamino}-pentyl)-ureido]-pentanedioic acid (L4)

Compound 10 was prepared following a published procedure (Mueller, C.; et al. *J Organometal Chem* 2004, 689, 4712-4721). Compound 11 was prepared as follows: to a solution of compound 10 (0.517 g, 1.7 mmol) in 10 mL of CH$_2$Cl$_2$ was added a solution of glyoxylic acid monohydrate (1.55 g, 1.68 mmol in 1 mL of MeOH containing activated molecular sieves) and was stirred for 30 min. Sodium triacetoxyborohydride (0.712 g, 3.3 mmol) was added to the solution in small portions and stirred overnight at ambient temperature. Product isolation (CH$_2$Cl$_2$, water, NaCl, Na$_2$SO$_4$) afforded crude compound that was used in the next step without further purification. Yield: 0.483 g, 1.32 mmol, 78.6%. TLC R$_f$=0.37 (10/90 MeOH/CH$_2$Cl$_2$). $^1$H NMR (CDCl$_3$) δ: 8.62 (m, 1H), 7.75 (m, 1H), 7.32 (m, 2H), 4.56 (bs, 1H), 4.04 (s, 2H), 3.46 (s, 2H), 3.14 (m, 2H), 2.78 (m, 2H), 2.09 (m, 1H), 1.74-1.16 (m, 16H). ESIMS m/z: 366.7 [M+1], 388.5 [M+Na]. The removal of t-Boc was performed by dissolving the crude compound (0.483 g, 1.32 mmol) in an ice-cold solution of 10 mL 1/1 TFA/CH$_2$Cl$_2$. The reaction mixture was allowed to stir at room temperature for 4 h. The solution was evaporated under reduced pressure and dried under vacuum to provide a colorless solid of 11 and was used without further purification. Yield: 0.315 g, 1.19 mmol, 90%. $^1$H NMR (MeOH-d$_4$) δ: 8.52 (d, J=5.6 Hz 1H), 7.78 (t, J=7.6 Hz, 1H), 7.54 (d, J=7.4 Hz, 1H), 7.29 (t, J=7.2 Hz, 1H), 3.78 (s, 2H), 3.22 (s, 2H), 2.85 (t, J=8.0 Hz, 2H), 2.5 (t, 2H), 1.72-1.20 (m, 8H). ESIMS m/z: 266.3 [M+1]$^+$, 288.3 [M+Na]$^+$. Compound L4 was prepared by coupling compound 6 with compound 11. Compound L4 was purified by HPLC using 76/24 water (0.1% TFA)/CH$_3$CN (0.1% TFA) as the mobile phase, flow rate: 2 mL/min, R$_t$=10.2 min. $^1$H NMR (D$_2$O) δ: 8.62 (d, J=5.6 Hz, 1H), 8.15 (t, J=6.4 Hz, 1H), 7.95 (d, J=7.6 Hz, 1H), 7.88 (t, J=6.4 Hz, 1H), 4.25 (m, 1H), 4.23-4.1 (m, 2H), 3.35 (m, 2H), 3.25-3.31 (m, 5H), 2.84 (m, 1H), 2.52 (t, J=6.8 Hz, 2H,) 2.27 (m, 6H), 1.64-1.21 (m, 23H). ESIMS m/z: 723 [M+1]$^+$ and 745.7 for [M+Na]$^+$, HRFAB$^+$-MS: Calcd for C$_{35}$H$_{55}$N$_6$O$_{11}$ 723.3929 [M+1], found 723.3912.

Example 6

2-(3-{5-[8-(Bis-pyridin-2-ylmethyl-amino)-octanoylamino]-1-carboxy-pentyl}-ureido)-pentanedioic acid (L5)

To a solution of 8-(bis-pyridin-2-ylmethyl-amino)-octanoic acid ((Levadala, et al. *Synthesis* 2004, 11, 1759-1766)) (0.9 g, 2.6 mmol, 15 mL DMF) was added O-benzotriazol-1-yl-N,N,N',N'-tetramethyluronium hexafluorophosphate (1.49 g, 3.9 mmol) and N-hydroxysuccinimide (0.36 g, 3.1 mmol). The reaction mixture was stirred at room temperature for 16 h. After removing solvent under reduced pressure, the crude product was purified by flash chromatography (10/90 MeOH/CH$_2$Cl$_2$) to give 12 as a thick, colorless liquid. Yield: 0.75 g, 0.17 mmol, 65%. $^1$H NMR (CDCl$_3$) δ: 8.58 (d, J=4.8 Hz, 2H), 7.78 (t, J=8.0 Hz, 2H), 7.50 (d, J=7.6 Hz, 2H), 7.32 (t, J=8.0 Hz, 2H), 4.62 (s, 4H), 3.27 (t, J=7.6 Hz, 2H), 2.82 (s, 4H), 2.58 (d, J=7.2 Hz, 2H), 1.82-1.66 (m, 4H), 1.33-1.28 (m, 6H). ESIMS: 439 [M+1]$^+$. To a solution of 12 (0.052 g, 0.11 mmol in 7 mL CH$_2$Cl$_2$) was added 5, (0.1 g, 0.11 mmol) followed by NEt$_3$ (0.2 mL, 1.4 mmol). The reaction mixture was stirred at room temperature for 5 h then concentrated under reduced pressure. Product isolation (EtOAc, water, NaCl, Na$_2$SO$_4$) followed by flash chromatography (50/50 MeOH/CH$_2$Cl$_2$) afforded pure compound the 4-methoxybenzyl ester of L5 in 51% (0.060 g, 0.056 mmol) yield. Cleavage of the PMB groups by stirring for 2 h in 1/1 TFA/CH$_2$Cl$_2$ followed by removal of solvent gave a solid residue. The residue was dissolved in 7 mL water, washed with 3×10 mL CH$_2$Cl$_2$ and the water layer concentrated under vacuum to provide crude L5. The compound was further purified by HPLC with 80/20 water (0.1% TFA)/CH$_3$CN (0.1% TFA) solution as the mobile phase. The flow rate was 3 mL/min, R$_f$=8 min. $^1$H NMR (D$_2$O) δ: 8.74 (d, J=6.0 Hz, 2H); 8.52 (t, J=8.0 Hz, 2H), 8.04 (d, J=8.0 Hz, 2H), 7.95 (t, J=6.4 Hz, 2H), 4.32 (s, 4H), 4.23 (s, 1H), 4.14 (s, 1H), 3.24 (t, J=6.4 Hz, 2H), 2.67 (t, J=7.6 Hz, 2H), 2.49 (t, J=7.2 Hz, 2H), 2.16 (m, 3H), 1.95 (m, 1H), 1.79 (m, 1H), 1.68 (m, 1H), 1.6-1.0 (m, 14H). ESIMS m/z: 643 [M+1]$^+$; HRFAB$^+$-MS: Calcd. for C$_{32}$H$_{47}$N$_6$O$_8$, 643.3455 [M+1], found 643.3463.

Example 7

2-{3-[5-(Bis-pyridin-2-ylmethyl-amino)-1-carboxy-pentyl]-ureido}-pentanedioic acid (L6)

To a solution of pyridine-2-aldehyde (50 mg, 0.44 mmol in 4 mL CH$_2$Cl$_2$) was added a solution of 1 (100 mg, 0.147 mmol in 4 mL CH$_2$Cl$_2$). This was stirred at ambient temperature for 2 h. The reaction mixture was cooled to 0° C. and sodium triacetoxyborohydride (93 mg, 0.44 mmol) was then added, with stirring for an additional 3 h while warming to ambient temperature. Product isolation (CH$_2$Cl$_2$, water, NaCl, Na$_2$SO$_4$) followed by flash chromatography (10/90 MeOH/CH$_2$Cl$_2$) afforded a colorless solid as the tri-PMB ester of L6. Removal of the PMB groups was effected by dissolving in 5 mL of 50/50 TFA/CH$_2$Cl$_2$ and was stirred at room temperature for 2 h. The resulting solution was concentrated to provide a colorless solid. The solid was dissolved in 3 mL water and washed with 5×5 mL CH$_2$Cl$_2$. The water layer was concentrated to provide a solid. Yield: 132 mg, 0.26 mmol, 61%. The product was purified by HPLC using 85/15 water (0.1% TFA)/CH$_3$CN (0.1% TFA) solution as mobile phase. Flow rate was 3 mL/min, R$_f$=13 min. $^1$H NMR (D$_2$O): 8.78 (d, J=5.2 Hz, 2H), 7.89 (t, J=7.7 Hz, 2H), 7.49 (d, J=7.6 Hz, 2H), 7.34 (t, J=6.4 Hz, 2H), 4.75-4.62 (m, 4H), 4.45-4.22 (m, 2H), 2.75 (m, 2H), 2.55 (t, J=6.6 Hz, 2H), 2.2-1.01 (m, 7H). ESIMS: 502 [M+1]$^+$, HRFAB$^+$: for C$_{24}$H$_{31}$N$_5$O$_7$ calcd: 501.2224 found: 502.2296.

Example 8

2-[3-(5-{7-[6-(Bis-pyridin-2-ylmethyl-amino)-hexyl-carbamoyl]-heptanoylamino}-1-carboxy-pentyl)-ureido]-pentanedioic acid (L7)

Compound L7 was prepared by reacting 13 (Levadala, et al. *Synthesis* 2004, 11, 1759-1766) with 6 similarly as described above for L1. HPLC purification was performed using 75/25 water (0.1% TFA)/CH$_3$CN (0.1% TFA) as mobile phase, flow rate 3 mL/min, R$_f$=5.5 min. $^1$H NMR (D$_2$O) δ: 8.65 (d, J=5.2 Hz, 2H), 7.99 (t, J=8.6 Hz, 2H), 7.59-7.54 (m, 4H), 4.59 (s, 4H), 4.21-4.14 (m, 2H), 3.29-3.17 (m, 7H), 2.48 (t, J=7.6 Hz, 2H), 2.27-2.22 (m, 6H), 1.82-1.32 (m, 19H). ESIMS m/z: 756 [M+1]$^+$; HRFAB$^+$-MS: Calcd. for C$_{38}$H$_{55}$N$_7$O$_{11}$, 756.4296 [M+1] found: 756.4032. All rhenium compounds were synthesized as for ReL1, for which a detailed example is provided below.

Example 9

Tricarbonyl(2-[3-(5-{7-[5-(bis-pyridin-2-ylmethyl-amino)-1-carboxy-pentylcarbamoyl]-heptanoylamino}-1-carboxy-pentyl)-ureido]-pentanedioic acid) rhenium bromide (ReL1)

Compound L1 (0.058 g, 0.074 mmol) was dissolved in 10 mL of water. A solution of [Re(CO)$_3$(H$_2$O)$_3$]Br$^{37}$ (0.029 mg in 0.5 mL methanol) was added and the reaction mixture was refluxed for 4 h. The solution was concentrated to provide a colorless solid that was washed with 3×10 mL diethyl ether, 3×10 mL CH$_2$Cl$_2$ and finally with water. Products were dried under vacuum and purified by HPLC method 1. R$_f$=12 min. $^1$H NMR (5/1 D$_2$O/CH$_3$CN) δ: 9.31 (d, J=5.4 Hz, 2H,), 8.64 (t, J=8 Hz, 2H), 7.88 (d, J=8 Hz, 2H), 7.85 (t, J=8 Hz, 2H,), 5.25-5.18 (m, 4H), 4.26 (m, 2H), 3.61 (t, J=5.2 Hz, 2H), 2.75 (t, J=6.4 Hz, 2H), 2.66 (t, J=7.2 Hz, 2H), 2.55-2.45 (m, 27H). ESIMS m/z: 1056 [M$^+$]; HRFAB$^+$-MS: Calcd for C$_{41}$H$_{55}$N$_7$O$_{14}$Re [M$^+$], 1056.3364 found: 1056.3350 [M$^+$]. IR ν (cm$^{-1}$) [Re(CO)$_3$]$^+$: 2030, 1912.

Example 10

Tricarbonyl(2-[3-(5-{7-[5-(bis-quinolin-2-ylmethyl-amino)-1-carboxy-pentylcarbamoyl]-heptanoylamino}-1-carboxy-pentyl)-ureido]-pentanedioic acid) rhenium bromide (ReL2)

For HPLC purification, method 2 was used. R$_f$=16 min. $^1$H NMR (1/1 D$_2$O/CD$_3$CN): 8.81-8.74 (m, 4H), 8.30 (d, J=8.0 Hz, 2H), 8.16 (t, J=8.0 Hz, 2H), 7.99 (t, J=7.2 Hz, 2H), 7.90 (d, J=8.0 Hz, 2H), 5.42-5.37 (m, 2H), 5.38-5.22 (m, 2H), 4.68-4.64 (m, 1H), 4.53-4.51 (m, 1H), 4.45-4.42 (m, 1H), 4.06-4.04 (m, 2H), 3.37 (t, J=6.8 Hz, 2H), 2.72 (t, J=7.2 Hz, 2H), 2.51 (t, J=7.2 Hz, 2H), 2.40-1.30 (bm, 24H). ESIMS m/z: 1156 [M]$^+$; HRFAB$^+$-MS: Calcd. for C$_{49}$H$_{59}$N$_7$O$_{14}$Re [M]$^+$, 1156.3677 found, 1156.3662 [M$^+$]. IR ν (cm$^{-1}$) [Re(CO)$_3$]$^+$: 2028, 1900.

Example 11

Tricarbonyl(2-[3-(5-{7-[5-(bis-pyridin-2-ylmethyl-amino)-5-carboxy-pentylcarbamoyl]-heptanoylamino}-1-carboxy-pentyl)-ureido]-pentanedioic acid)rehenium bromide (ReL3)

For HPLC purification method 3 was used. Flow rate was 2 mL/min, R$_f$=11.5 min. $^1$H NMR (5/1 D$_2$O/CH$_3$CN) δ: 9.26 (d, J=5.6 Hz, 1H), 9.20 (d, J=5.6 Hz, 1H), 8.36 (t, J=8.0 Hz, 2H), 7.90 (m, 2H), 7.83 (m, 2H), 5.31-5.03 (m, 4H), 3.67 (t, J=6.8 Hz, 2H), 3.53 (t, J=6.6 Hz, 2H), 3.15 (t, 2H), 2.40-1.30 (bm, 29H). ESIMS m/z: 1056 [M]$^+$; HRFAB$^+$-MS: Calcd for C$_{41}$H$_{55}$N$_7$O$_{14}$Re [M]$^+$, 1056.3364 found: 1056.3350[M$^+$].

Example 12

Tricarbonyl(2-[3-(1-carboxy-5-{7-[6-(carboxymethyl-pyridin-2-ylmethyl-amino)-hexylcarbamoyl]-heptanoylamino}-pentyl)-ureido]-pentanedioic acid) rhenium (ReL4)

For HPLC purification, method 1 was used. $R_t$=18 min. ($D_2O$:$CH_3CN$(5:1)) δ: 9.29 (d, J=5.6 Hz, 1H), 9.22 (d, J=8.0 Hz, 1H), 8.88 (d, J=8.0 Hz, 1H), 7.84 (t, J=8.0 Hz, 1H), 5.31-5.03 (m, 2H), 4.67 (m, 2H), 4.25 (m, 2H), 3.53 (m, 2H), 3.35 (t, J=7.8 Hz, 2H), 2.72 (m, 2H), 2.46-1.30 (bm, 30H). ESIMS m/z: 993 [M+1]$^+$, HRFAB$^+$-MS: Calcd for $C_{37}H_{54}N_6O_{14}Re$ 993.3255 [M+1]$^+$, found 993.3237.

Example 13

Tricarbonyl(2-(3-{5-[8-(bis-pyridin-2-ylmethyl-amino)-octanoylamino]-1-carboxy-pentyl}-ureido)-pentanedioic acid)rhenium bromide (ReL5)

For HPLC purification, method 1 was used. $R_t$=17 min. $^1$H NMR (5/1 $D_2O$/$CH_3CN$) δ: 9.23 (d, J=5.6 Hz, 2H), 8.34 (t, J=8.0 Hz, 2H), 7.72 (d, J=8 Hz, 2H), 7.77 (t, J=6.4 Hz, 2H), 5.13 (m, 4H), 4.66 (m, 1H), 4.58 (m, 1H), 4.16 (m, 2H), 3.56 (t, J=6.8 Hz, 2H), 2.86 (t, J=7.6 Hz, 2H), 2.59-1.6 (m, 20H). ESIMS m/z: 913[M]$^+$, HRFAB$^+$-MS: Calcd for $C_{35}H_{46}N_6O_{11}Re$, [M]$^+$ 914.2860, found 914.2833.

Example 14

Tricarbonyl(2-{3-[5-(bis-pyridin-2-ylmethyl-amino)-1-carboxy-pentyl]-ureido}-pentanedioic acid)rhenium bromide (ReL6)

For HPLC purification, method 1 was used. $R_t$=10.1 min. $^1$H NMR ($CD_3CN$) δ: 9.12 (d, J=5.6 Hz, 2H), 8.22 (t, J=7.7 Hz, 2H), 7.80 (d, J=8.0 Hz, 2H), 7.65 (t, J=6.5 Hz, 2H), 5.03 (m, 4H), 4.59-4.58 (m, 2H), 4.08 (m, 2H), 2.79 (t, J=7.6 Hz, 2H), 2.34-2.24 (m, 6H), 1.82-1.80 (m, 2H). ESIMS: 502 [M]$^+$, HRFAB$^+$: Calcd for $C_{72}H_{31}N_5O_{10}Re$, 772.1628, found 772.1632.

Example 15

Tricarbonyl(2-[3-(5-{7-[6-(Bis-pyridin-2-ylmethyl-amino)-hexylcarbamoyl]-heptanoylamino}-1-carboxy-pentyl)-ureido]-pentanedioic acid)rhenium bromide (ReL7)

For HPLC purification, method 1 was used. $R_t$=18.0 min. $^1$H NMR (5/1 $D_2O$/$CD_3CN$) δ: 9.43 (d, J=5.2 Hz, 2H), 8.56 (t, J=8.6 Hz, 2H), 8.10 (d, J=7.6 Hz, 2H), 7.97 (t, J=6.4 Hz, 2H), 5.38-5.29 (m, 4H), 4.80-4.35 (m, 2H), 3.80-3.72 (m, 5H), 3.05 (t, J=7.6 Hz, 2H), 2.8-1.82 (m, 27H).

Example 16

2-{3-[1-Carboxy-5-(7-{1-carboxy-5-[2-(4,7,10-tris-carboxymethyl-1,4,7,10tetraaza-cyclododec-1-yl)-acetylamino]-pentylcarbamoyl}-heptanoylamino)-pentyl]ureido}-pentanedioic acid (DOTA-L1)

A solution of H-Lys(Boc)-OtBu (0.30 g, 0.107 mmol in 0.5 mL DMF) was added to a stirred solution of 6 (0.100 g, 0.107 mmol in 5 mL dry DMF) at room temperature followed by the addition of 0.2 mL $NEt_3$. The reaction mixture was stirred for 10 h at room temperature. The reaction mixture was then concentrated under reduced pressure. Product isolation ($CH_2Cl_2$, water, $Na_2SO_4$) followed by flash chromatography (10/90 MeOH/$CH_2Cl_2$) afforded the compound compound 14 as a colorless solid in 74% yield (0.090 g, 0.08 mmol). TLC $R_f$=0.45 (10/90 MeOH/$CH_2Cl_2$). ESIMS m/z: 1186.5 [M+1]$^+$. The compound 14 (20 mg, 0.017 mmol) was dissolved in an ice-cold solution of TFA (2 mL) and $CH_2Cl_2$ (2 mL) and was stirred for 10 min. The ice bath was removed and the solution was allowed to warm to room temperature with continued stirring for 1 hr. The solution was evaporated under reduced pressure and the light brown residue was dried under high vacuum for 2 h. The residue was washed with diethyl ether (3×5 mL) and water (10×2 mL) to produce crude urea compound 16. Yield: 9 mg, 0.015 mmol, 88%. The colorless product was dried under vacuum and purified further by HPLC using 86/14 water (0.1% TFA)/acetonitrile (0.1% TFA) as mobile phase, flow rate 4 ml/min; $R_t$=6 min. $^1$H NMR ($D_2O$) δ: 4.32-4.18 (m, 3H), 3.30 (t, 1H), 3.05 (m, 1H), 2.54 (t, J=6 Hz, 2H), 2.35 (m, 2H), 2.21 (t, J=7.6 Hz, 2H), 2.10-1.18 (m, 15H). ESIMS m/z: 604.5 [M+1]$^+$. To the compound 16 (9 mg, 0.015 mmol in 300 μl PBS buffer, pH 7.2) was added DOTA-NHS (purchased from Macrocyclics, TX, USA) (0.039 mmol) and the solution was stirred for 3 hr at rt. The crude product was purified via HPLC using 86/14 water (0.1% TFA)/acetonitrile (0.1% TFA) as mobile phase, flow rate 4 ml/min; $R_t$=9 min. $^1$H NMR ($D_2O$) δ: 4.32-4.18 (m, 3H), 3.90-3.05 (m, 16H), 2.54 (t, J=6 Hz, 2H), 2.21 (m, J=7.6 Hz, 4H), 2.10-1.11 (m, 34H). ESIMS m/z: 990 [M+1]$^+$. HRFAB$^+$-MS: Calcd. for $C_{42}H_{72}N_9O_{18}$, 990.4995 [M+1], found: 990.5100. IC$_{50}$: 0.8 nM.

In-111 labeling: 800 μCi of $^{111}InCl_3$ in 0.2 N HCl was incubated with 100 μl of 0.2 M sodium acetate buffer so that final pH of the solution was ~5.5 at 90° C. for 45 min. Radiolabeled product was purified via HPLC using 90/10 water (0.1% TFA)/acetonitrile (0.1% TFA) as mobile phase, flow rate 4 ml/min; $R_t$=18 min. Radiolabeling yield was 50%, and radiochemical purity was >95%.

Example 17

Radiochemistry

Compounds L1-L7 were synthesized in radioactive ($^{99m}$Tc-labeled) form using the same general method as described below for [$^{99m}$Tc]L1. All Tc-99m-labeled compounds were synthesized in radiochemical yields of >70% and radiochemical purities of >98%.

[$^{99m}$Tc(CO)$_3$(H$_2$O)$_3$]$^+$ preparation, typical example: 11.2 mCi (in 1 mL saline) $^{99m}$TcO$_4$$^-$ was added to the Isolink kit and the reaction mixture was heated in a water bath at 95° C. for 30 min then allowed to cool to room temperature. $^{99m}$TcL preparation, typical example: 500 μL of the [$^{99m}$Tc(CO)$_3$(H$_2$O)$_3$]$^+$ solution (2.3 mCi) was neutralized with 50 μL 1(N) HCl. To this was added a 200 μL of phosphate-buffered saline (PBS) solution and 300 μL of a solution of L1 (4 mg, 5.09 μmol in 2.5 mL water). This was kept at 95° C. for 30 min. The vial was cooled for 5 min at room temperature. This was diluted with 750 μL of the HPLC mobile phase and purified by radio-HPLC (Method 1). The major radioactive peak constituting desired product (1.6 mCi) eluted at 14 min. The acidic eluate was neutralized with 100 μL 0.1M NaHCO$_3$ solution and the volume was reduced to 400 μL, pH 8 under reduced pressure. This was diluted with PBS to the desired radioactivity concentration for ex vivo biodistribution and imaging studies. Radiochemical yield [$^{99m}$Tc]L1: 82.05%. Radiochemical purity=98.99%.

Example 18

Fluorescence Spectra

Fluorescence spectra were recorded using a Varian Cary Eclipse fluorescence spectrophotometer using with 321 nm excitation from a Xenon arc lamp. Compound ReL2 was dissolved in ethylene glycol. Measurements were performed under air or after argon purging of the solution. Lifetime measurements were performed using a Model D2, ISS, Inc. frequency domain spectrofluorimeter. The excitation wavelength was 370 nm from the UV LED. The fluorescence intensity data were collected through a bandpass filter in the spectral region 540-600 nm. Luminescence quantum yields were measured by the optical dilute method (Nakamura, K. *Bull Chem Soc Japn* 1982, 55, 2697-2705) using an aerated aqueous solution of [Ru(bpy)$_3$]Cl$_2$ (φ=0.028, excitation wavelength at 455 nm) as the standard solution (Crosby, G. A.; Demas, J. N. *J Phys Chem* 1971, 75, 991-1024).

Example 19

NAALADase Assay

NAAG hydrolysis was performed essentially as described previously (Robinson, M. B.; et al. *J Biol Chem* 1987, 262, 14498-14506; Lupold, S. E.; et al. *Cancer Res* 2002, 62, 4029-4033.). In short, LNCaP cell extracts were prepared by sonication in NAALADase buffer [50 mM Tris (pH 7.4) and 0.5% Triton X-100]. Cell lysates were incubated with or without inhibitor at 37° C. for 10 minutes. Following the incubation the radiolabeled substrate N-acetyl-L-aspartyl-L-(3,4-$^3$H)glutamate (NEN Life Science Products, Boston, Mass.) was added to a final concentration of 30 nM at 37° C. for 10-15 min. The reaction was stopped by the addition of an equal volume of ice-cold 100 mM sodium phosphate and 2 mM EDTA. Products were partitioned by AG 1-X8 formate resin (Bio-Rad Laboratories) anion exchange chromatography, eluted with 1 M sodium formate, and quantified by liquid scintillation counting. Inhibition curves were determined using semi-log plots and IC$_{50}$ values determined at the concentration at which enzyme activity was inhibited by 50%. Assays were performed in triplicate with the entire inhibition study being repeated at least once to confirm affinity and mode of inhibition. Data were collected during linear phase of hydrolysis (i.e., <20% cleavage of total substrate). Enzyme inhibitory constants (K$_i$ values) were generated using the Cheng-Prusoff conversion (Cheng, Y.; Prusoff, W. H. *Biochem Pharmcol* 1973, 22, 3099-3108).

TABLE 1

PSMA inhibitory activity and calculated ClogD.

|  | Ki[nM] | 95% CI* | ClogD |
|---|---|---|---|
| L1 | 15.25 | 7.93 | -7.69 |
| ReL1 | 10.75 | 3.81 |  |
| L2 | 0.17 | 0.05 | -3.91 |
| ReL2 | 0.50 | 0.07 |  |
| L3 | 1.08 | 0.14 | -7.19 |
| ReL3 | 10.34 | 3.76 |  |
| L4 | 2.54 | 0.60 | -6.13 |
| ReL4 | 0.17 | 0.08 |  |
| L5 | 1.86 | 0.21 | -5.05 |
| ReL5 | 0.91 | 0.44 |  |
| L6 | 7.53 | 5.65 | -6.25 |
| ReL6 | 199.56 | 135.26 |  |
| L7 | 0.45 | 0.25 | -5.61 |
| ReL7 | 2.06 | 0.25 |  |
| PMPA | 0.20 | 0.06 | -8.65 |

*confidence interval

Example 20

Cell Culture and Ex Vivo Biodistribution

PSMA+ PC3 PIP cells (human metastatic [bone] prostate carcinoma) engineered to express PSMA stably and PSMA− PC3 flu cells were generously provided by Warren Heston (Cleveland Clinic). Cells were cultured in T175 flasks using RPMI 1640 medium (Sigma) supplemented with 10% FBS and Penicillin/Streptomycin (100 U/mL/100 µg/mL) at 37° C. in 5% CO$_2$ in air. When a sufficient number of cells were present in culture, the cells were trypsinized and formulated in sterile Hanks buffered saline solution (Sigma, HBSS) and counted using a hemocytometer and trypan blue dye to confirm cell viability. Typically, 2-5×10$^6$ cells were injected subcutaneously such that PC3 PIP cells were injected behind the left shoulder and PC3 flu cells were inject behind the right shoulder of male severe-combined immunodeficient mice (SCID). All in vivo experimental procedures were undertaken in compliance with United States laws governing animal experimentation and were approved by the Johns Hopkins University Institutional Animal Care and Use Committee. Mice were used when the tumors reached 3-7 mm in diameter for either ex vivo biodistribution studies or in vivo SPECT-CT.

The xenograft-bearing mice (17-20 g) were injected via the tail vein with 3.70 MBq (100 µCi) of [$^{99m}$Tc]L1-4 in 200 µL of saline. Blood was collected immediately after sacrifice (cervical dislocation) by cardiac puncture and heart, lung, liver, stomach, pancreas, spleen, white fat, kidney, muscle, small intestine, large intestine, urinary bladder, tumor xenografts were harvested, weighed and counted in an automated gamma counter (LKB Wallace 1282 Compugamma CS Universal Gamma Counter). Animals were sacrificed at 30, 60, 120 and 300 min post-injection (n=4 per time point). Tissue radiopharmaceutical uptake values were calculated as percent injected dose per gram (% ID/g) as compared with a 1:10 diluted standard dose. The urinary bladder was emptied and water washed and then dried prior to weighing and counting.

TABLE 2

Biodistribution of [$^{99m}$Tc]L1 in tumor bearing mice

| | 30 min. | 60 min. | 120 min. | 300 min. |
|---|---|---|---|---|
| Blood | 0.54 ± 0.39 | 0.11 ± 0.04 | 0.02 ± 0.01 | 0.01 ± 0.00 |
| heart | 0.19 ± 0.13 | 0.04 ± 0.02 | 0.02 ± 0.01 | 0.01 ± 0.00 |
| lung | 0.64 ± 0.23 | 0.18 ± 0.06 | 0.05 ± 0.00 | 0.04 ± 0.06 |
| liver | 1.49 ± 1.12 | 0.25 ± 0.15 | 0.08 ± 0.04 | 0.04 ± 0.01 |
| stomach | 0.35 ± 0.15 | 0.17 ± 0.00 | 0.41 ± 0.61 | 0.03 ± 0.01 |
| pancreas | 0.18 ± 0.10 | 0.05 ± 0.02 | 0.01 ± 0.01 | 0.00 ± 0.00 |
| spleen | 10.59 ± 6.05 | 1.81 ± 1.10 | 0.59 ± 0.29 | 0.07 ± 0.04 |
| fat | 0.36 ± 0.14 | 0.11 ± 0.03 | 0.05 ± 0.07 | 0.01 ± 0.00 |
| kidney | 95.66 ± 22.06 | 68.54 ± 8.32 | 10.08 ± 5.71 | 1.26 ± 0.67 |
| muscle | 0.39 ± 0.12 | 0.25 ± 0.15 | 0.056 ± 0.04 | 0.04 ± 0.05 |
| small intestine | 5.87 ± 2.35 | 1.29 ± 0.76 | 0.38 ± 0.13 | 0.03 ± 0.01 |
| large intestine | 2.28 ± 2.03 | 16.02 ± 12.39 | 1.30 ± 2.00 | 0.10 ± 0.09 |
| bladder | 2.31 ± 0.88 | 2.19 ± 1.78 | 5.01 ± 8.18 | 0.80 ± 1.33 |
| PC-3 PIP | 7.87 ± 3.95 | 3.86 ± 0.57 | 2.31 ± 0.84 | 0.84 ± 0.51 |
| PC-3 flu | 0.34 ± 0.15 | 0.16 ± 0.08 | 0.05 ± 0.02 | 0.01 ± 0.01 |
| PIP: muscle | 20 | 15 | 41 | 23 |
| flu: muscle | 0.9 | 0.6 | 0.9 | 0.3 |
| PIP: flu | 23 | 25 | 44 | 68 |

Values expressed are in % ID/g ± standard deviation. N = 4 for all tissues.

TABLE 3

Biodistribution of [$^{99m}$Tc]L2 in tumor bearing mice

| | 30 min. | 60 min. |
|---|---|---|
| Blood | 0.28 ± 0.05 | 0.36 ± 0.11 |
| heart | 0.23 ± 0.01 | 0.22 ± 0.06 |
| lung | 0.82 ± 0.17 | 0.69 ± 0.14 |
| liver | 1.75 ± 0.40 | 1.15 ± 0.33 |
| stomach | 0.45 ± 0.12 | 0.36 ± 0.30 |
| pancreas | 0.35 ± 0.20 | 0.34 ± 0.16 |
| spleen | 10.36 ± 9.64 | 15.32 ± 6.64 |
| kidney | 47.86 ± 8.88 | 86.02 ± 13.93 |
| muscle | 0.54 ± 0.27 | 0.26 ± 0.11 |
| small intestine | 5.22 ± 1.92 | 2.35 ± 1.90 |
| large intestine | 1.25 ± 1.21 | 0.53 ± 0.42 |
| bladder | 0.46 ± 0.31 | 0.39 ± 0.18 |
| PC-3 PIP | 1.09 ± 0.61 | 2.04 ± 0.25 |
| PC-3 flu | 0.34 ± 0.18 | 0.46 ± 0.17 |
| PIP: muscle | 2 | 8 |
| flu: muscle | 0.6 | 2 |
| PIP: flu | 3 | 4 |

Values in percent injected dose per gram ± Standard deviation. N = 4 for all tissues.

TABLE 4

Biodistribution of [$^{99m}$Tc]L3 in tumor bearing mice

| | 30 min. | 60 min. | 120 min. | 300 min. |
|---|---|---|---|---|
| Blood | 0.68 ± 0.19 | 1.81 ± 1.61 | 0.08 ± 0.05 | 0.02 ± 0.00 |
| heart | 0.51 ± 0.13 | 1.56 ± 1.05 | 0.04 ± 0.01 | 0.04 ± 0.01 |
| lung | 2.48 ± 0.95 | 3.14 ± 1.82 | 0.13 ± 0.01 | 0.07 ± 0.00 |
| liver | 1.47 ± 0.14 | 2.85 ± 1.85 | 0.22 ± 0.05 | 0.17 ± 0.01 |
| stomach | 0.74 ± 0.15 | 3.87 ± 3.02 | 0.36 ± 0.19 | 0.12 ± 0.06 |
| pancreas | 0.61 ± 0.14 | 5.71 ± 4.68 | 0.12 ± 0.08 | 0.05 ± 0.00 |
| spleen | 32.07 ± 16.36 | 25.90 ± 10.08 | 0.98 ± 0.25 | 0.42 ± 0.07 |
| fat | 0.59 ± 0.17 | 4.67 ± 5.89 | 0.04 ± 0.01 | 0.02 ± 0.00 |
| kidney | 163.57 ± 29.62 | 178.56 ± 35.45 | 29.87 ± 27.09 | 1.91 ± 0.45 |
| muscle | 0.92 ± 0.25 | 1.42 ± 1.32 | 0.73 ± 0.25 | 0.04 ± 0.01 |
| small intestine | 10.62 ± 5.30 | 21.03 ± 4.46 | 0.58 ± 0.23 | 0.28 ± 0.20 |
| large intestine | 1.64 ± 0.71 | 6.49 ± 4.91 | 0.80 ± 0.40 | 0.53 ± 0.24 |
| bladder | 3.30 ± 1.06 | 10.38 ± 6.28 | 21.63 ± 35.22 | 0.43 ± 0.19 |
| PC-3 PIP | 11.56 ± 2.86 | 6.59 ± 5.22 | 1.89 ± 0.21 | 0.75 ± 0.55 |
| PC-3 flu | 0.53 ± 0.15 | 1.53 ± 1.69 | 0.32 ± 0.27 | 0.18 ± 0.17 |
| PIP: muscle | 13 | 5 | 3 | 18 |
| flu: muscle | 0.6 | 1 | 0.4 | 4 |
| PIP: flu | 23 | 4 | 6 | 4 |

Values in percent injected dose per gram ± standard deviation. N = 4 for all tissues.

Example 21

SPECT-CT Imaging of PC3 PIP and PC3 Flu Xenografts

Compounds L1-L4 were studied with imaging. Xenograft models were generated as described above. Mice were anesthetized using 1% isoflurane gas in oxygen flowing at 0.6 L/min prior to and during radiopharmaceutical injection. Mice were injected via the tail vein with approximately 480 µCi (17.76 MBq) of either L1, L2, L3 or L4 formulated in 200 µL of PBS, pH 7. Allowing for 15 min of radiopharmaceutical uptake, anesthetized mice were placed on the scanner gantry and secured with medical tape while the anesthetic flow was increased to 0.8 L/min. Body temperature of the mice was maintained by covering them with several layers of Chux disposable pads in addition to keeping them illuminated with a dissection lamp during scanning. A Gamma Medica (Northridge, Calif.) X-SPECT scanner equipped with two opposing low-energy 0.5 mm aperature pinholes and tunable CT was used for all scans. Mice were scanned over 180° in 5.5°, 30 second increments. A CT scan was performed prior to scintigraphy for both anatomical coregistration and attenuation correction. Data were reconstructed and fused using commercial software from the vendor (Gamma Medica), which includes a 2D-OSEM algorithm.

Example 22

In Vivo Binding Specificity (Blocking) Study

[$^{99m}$Tc]L1 [1.1 mCi (40.7 MBq)] in 200 µL of saline was administered via the tail vein to an anesthetized animal bearing an LNCaP (PSMA+) tumor. Concurrently a second animal, also bearing an LNCaP tumor, was administered a cocktail containing 1.2 mCi (44.4 MBq) of [$^{99m}$Tc]L1 and 1 mg of PMPA (Axxora Platform, San Diego, Calif.) in a total volume of 200 µL saline. SPECT-CT imaging was then performed as described above, with both animals on the scanner gantry.

Example 23

Metabolite Studies

Male CD-1 mice (Charles River Laboratories) were injected with 15 µCi (555 kBq) of [$^{99m}$Tc]L1 in saline via the tail vein. Mice were sacrificed at either 30 min or 1 h postinjection by cervical dislocation and their blood and selected organs were removed. Blood samples were withdrawn using heparinized syringes and tissues were placed on ice prior to manual homogenization in PBS, pH 7.4. Plasma and tissue homogenates in PBS were centrifuged for 2 min at 13,000×g at ambient temperature. A portion of the supernatant was diluted to 4 mL in 8 M urea containing 50 mg citric acid. Urine samples were added directly to 4 mL of the acidified urea solution. Samples then underwent separation by HPLC as previously described (Hilton, J.; et al. *Nucl Med Biol* 2000, 27, 627-630). Briefly, the 4 mL sample in 8 M acidified urea was passed through a capture column (Strata-X, 19×4.4 mm, Phenomenex, Torrance, Calif.) at 2 mL/min followed by 1% acetonitrile in water to wash plasma proteins from the column. The effluent from the capture column, containing only highly polar components, flowed through a dual BGO detector (Bioscan, Washington, D.C.) operating in the diode mode. The solvent was then switched to 30% acetonitrile:50 mM phosphate buffer at pH 2.4 (2 mL/min) for elution of the radiolabeled components previously bound to the capture column onto the analytical column (Synergi Polar-RP 250× 4.6 mm 10 micron particle size Phenomenex).

Example 24

In Vitro Fluorescence Microscopy of ReL2 in PC3 PIP and PC3 Flu Cells

Compound L2, when bound to the [Re(I)(CO)$_3$]$^+$ core, was hypothesized to be fluorescent as the corresponding bisquinoline chelator is known to have fluorescent properties (Banerjee, S. R.; et al. *Chem Commun (Camb)* 2005, 1784-1786; Stephenson, K. A.; et al. *J Am Chem Soc* 2004, 126, 8598-8599; James, S.; et al. *Bioconjug Chem* 2006, 17, 590-596; Banerjee, S. R.; et al. *Inorg Chim Acta* 2006, 359, 1603-1612). Following fresh preparation of ReL2, 10,000 PC3 PIP and PC3 flu cells were seeded separately into each of four wells of a Lab-Tek II 8-well chamber slide (Fisher Scientific). The cells were cultured as described above and were allowed to attach to the bottom of the wells overnight at 37° C. in 5% CO$_2$ in air. Serially diluted aliquots of ReL2 were added to the media in six of the wells such that wells contained 500 nM, 250 nM or 125 nM ReL2 with two remaining free of fluorophore. The cells were then returned to the incubator for one hour to enable binding. Each well was then carefully washed by removing the supernatant followed by addition of warm culture media for 30 seconds. The wash media was then removed and added to the contents of the well chambers. Dako Cytomation mounting medium was then applied and a glass coverslip was added. The mounting medium was allowed to dry at ambient temperature for 20 min prior to storage of the slide at 4° C. overnight. The cells were then viewed using an Olympus BX61 fluorescence microscope equipped with a Semrock DAPI/FITC/Texas Red triple filter cube. Excitation was at 494 nm with collection of emitted fluorescence at 628 nm.

What is claimed is:

1. A compound of formula II:

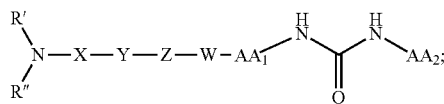

Wherein

AA$_1$ is lysine and AA$_2$ is glutamic acid;
R' is a substituted alkyl;
R" is a substituted alkyl;
X and Z are each independently C$_1$-C$_8$ alkylene, which may be substituted with 0-5 R$_A$;
W is C(=O);
Y is —NH—CO;
R$_A$, for each occurrence, is CO$_2$H.

2. The compound of claim 1, wherein the compound is a compound of formula V:

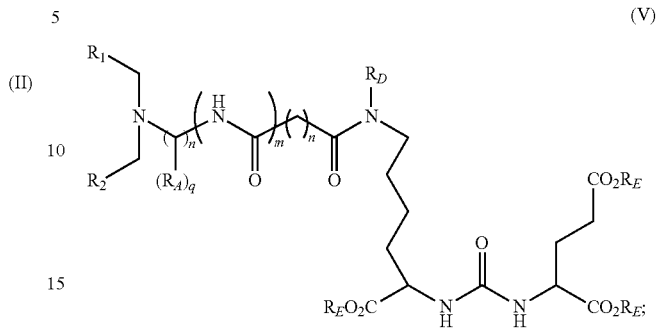

wherein
R$_D$ is H;
each R$_E$ is H;
R$_1$ is pyridyl or quinolinyl;
R$_2$ is pyridyl, quinolinyl or —COOH;
R$_A$, for each occurrence, is CO$_2$H;
m is 1; and
each n is independently 1-8;
and each q is independently 0 or 1.

3. The compound of claim 2, selected from the following:

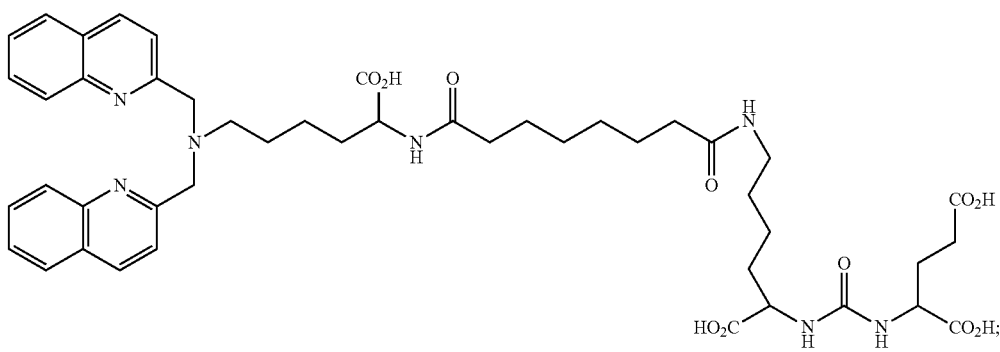

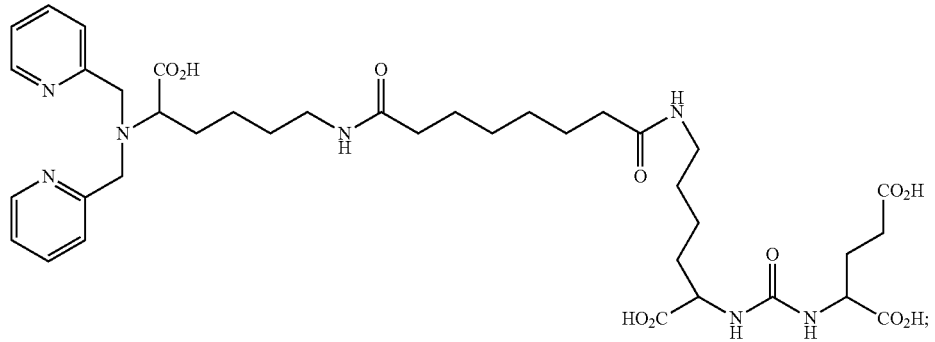
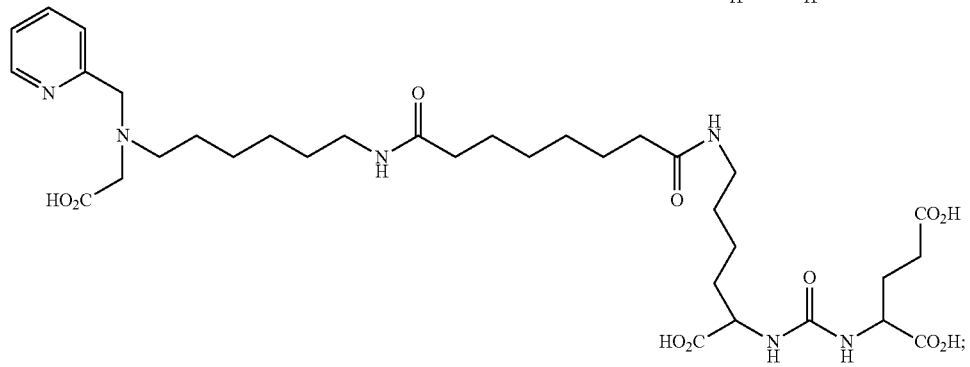
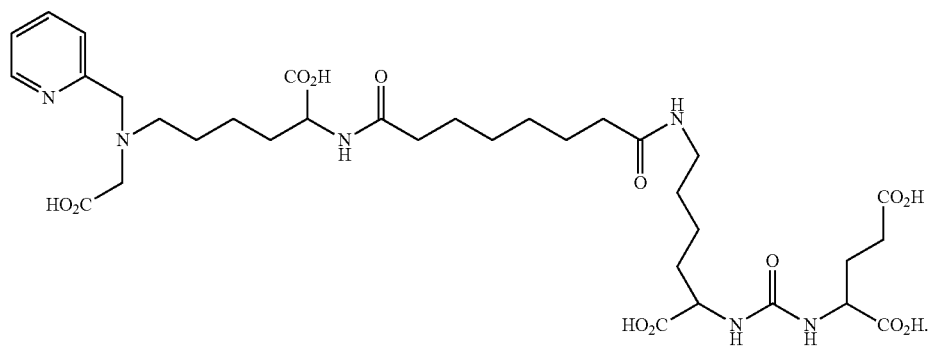
4. The compound of claim 1 further comprising a metal, of formula IX:
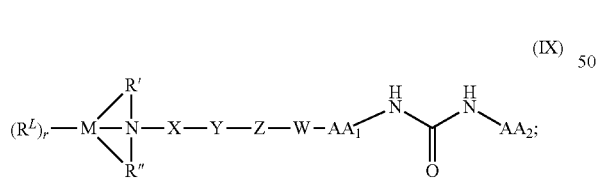
wherein
M is 99m-Tc or Re;
$AA_1$ is lysine and $AA_2$ is glutamic acid;
$R^L$ is CO;
R' is a substituted alkyl;
R" is a substituted alkyl;
X and Z are each independently $C_1$-$C_8$ alkylene, each of which may be substituted with 0-5 $R_A$;
Y is —NH—CO— and W is —C(=O)—;
$R_A$, for each occurrence, is $CO_2H$; and
r is 1-5.
* * * * *